(12) United States Patent
Yu et al.

(10) Patent No.: US 9,274,059 B2
(45) Date of Patent: Mar. 1, 2016

(54) MICROFLUIDIC ELECTROCHEMICAL DEVICE AND PROCESS FOR CHEMICAL IMAGING AND ELECTROCHEMICAL ANALYSIS AT THE ELECTRODE-LIQUID INTERFACE IN-SITU

(71) Applicants: Xiao-Ying Yu, Richland, WA (US); Bingwen Liu, Pullman, WA (US); Li Yang, Richland, WA (US); Zihua Zhu, Richland, WA (US); Matthew J. Marshall, Richland, WA (US)

(72) Inventors: Xiao-Ying Yu, Richland, WA (US); Bingwen Liu, Pullman, WA (US); Li Yang, Richland, WA (US); Zihua Zhu, Richland, WA (US); Matthew J. Marshall, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 324 days.

(21) Appl. No.: 14/050,144

(22) Filed: Oct. 9, 2013

(65) Prior Publication Data
US 2014/0038224 A1 Feb. 6, 2014

Related U.S. Application Data

(63) Continuation-in-part of application No. 13/047,025, filed on Mar. 14, 2011, now Pat. No. 8,555,710.

(51) Int. Cl.
*G01N 23/22* (2006.01)
*G01N 21/75* (2006.01)
*G01N 27/403* (2006.01)
*G01N 27/447* (2006.01)

(52) U.S. Cl.
CPC ............ *G01N 21/75* (2013.01); *G01N 23/2204* (2013.01); *G01N 27/403* (2013.01); *G01N 27/447* (2013.01)

(58) Field of Classification Search
CPC . G01N 2021/056; G01N 23/00; G01N 23/22; G01N 23/2204; G01N 23/08; G01N 23/09; G01N 23/083; G01N 23/12
USPC ........ 73/61.41, 64.55, 64.56, 865.6; 250/428, 250/430, 435, 438, 440.11; 356/436, 440; 850/9, 12, 14, 15
See application file for complete search history.

(56) References Cited

U.S. PATENT DOCUMENTS

| | | | |
|---|---|---|---|
| 6,758,961 B1 * | 7/2004 | Vogel ............... | G01N 33/48728 204/403.01 |
| 7,201,836 B2 * | 4/2007 | Vogel ............... | G01N 33/48728 204/403.01 |
| 7,204,139 B2 * | 4/2007 | Takayama ............. | B01F 5/0646 73/204.26 |

(Continued)

OTHER PUBLICATIONS

Somorjai, G. A., Molecular level studies of solid-gas and solid-liquid interfaces, Surface Science, 335, 1995, 10-22.

(Continued)

*Primary Examiner* — Peter Macchiarolo
*Assistant Examiner* — Nathaniel Kolb
(74) *Attorney, Agent, or Firm* — James D. Matheson

(57) ABSTRACT

A microfluidic electrochemical device and process are detailed that provide chemical imaging and electrochemical analysis under vacuum at the surface of the electrode-sample or electrode-liquid interface in-situ. The electrochemical device allows investigation of various surface layers including diffuse layers at selected depths populated with, e.g., adsorbed molecules in which chemical transformation in electrolyte solutions occurs.

24 Claims, 12 Drawing Sheets

(56) References Cited

U.S. PATENT DOCUMENTS

| | | | | |
|---|---|---|---|---|
| 7,244,349 | B2* | 7/2007 | Vogel | G01N 33/48728 204/403.01 |
| 7,387,715 | B2* | 6/2008 | Vogel | G01N 33/48728 204/403.01 |
| 8,555,710 | B2* | 10/2013 | Yu | G01N 23/2204 250/440.11 |
| 2006/0199260 | A1* | 9/2006 | Zhang | B01F 13/0059 435/293.1 |
| 2007/0231850 | A1* | 10/2007 | Geoffrey | C12M 25/02 435/29 |
| 2012/0234082 | A1* | 9/2012 | Yu | G01N 23/2204 73/61.41 |

OTHER PUBLICATIONS

Somorjai, G. A., et al., Impact of surface chemistry, PNAS, 108, 3, 2011, 917-924.
Stuve, E. M., et al., Relating the in-situ, ex-situ, and non-situ environments in surface electrochemistry, Surface Science, 335, 1995, 177-184.
Stuve, E. M., et al., Chemistry and physics of the "liquid"/solid interface: A surface science perspective, J. Vac. Sci. Technol. A, 11, 4, 1993, 2217-2224.
Somorjai, G. A., et al., Concepts, instruments, and model systems that enabled the rapid evolution of surface science, Surface Science, 603, 2009, 1293-1300.
Balasubramanian, M., et al., In situ X-ray diffraction and X-ray absorption studies of high-rate lithium-ion batteries, Journal of Power Sources, 92, 2001, 1-8.
Dowsett, M. G., et al., Cell for Simultaneous Synchrotron Radiation X-ray and Electrochemical Corrosion Measurements on Cultural Heritage Metals and Other Materials, Anal. Chem., 78, 2006, 3360-3365.
Foresti, M. L., et al., In situ X-ray analysis under controlled potential conditions: An innovative setup and its application to the investigation of ultrathin films electrodeposited on Ag(111), Electrochemica Acta, 51, 2006, 5532-5539.
Leriche, J. B., et al., An Electrochemical Cell for Operando Study of Lithium Batteries Using Synchrotron Radiation, Journal of the Electrochemical Society, 157, 5, 2010, A606-A610.
Roberts, G. A., Reflection-mode x-ray powder diffraction cell for in situ studies of electrochemical reactions, Review of Scientific Instruments, 75, 5, 2004, 1251-1254.
Scherb, G., et al., A novel thick-layer electrochemical cell for in situ x-ray diffraction, Review of Scientific Instruments, 69, 2, 1998, 512-516.
Scherb, G., et al., In situ x-ray standing-wave analysis of electrodeposited Cu monolayers on GaAs(001), Physical Review B, 58,, 16, 1998, 10800-10805.
Sherwood, P. M. A., Probing electrode surface chemical composition with core and valence band photoemission and an anaerob ic cell, Colloids and Surfaces A: Physicochemical and Engineering Aspects, 134, 1998, 221-230.
Warren, S., et al., X-ray structural analysis of semiconductor-electrolyte interfaces, World Scientific Publ Co Pte Ltd, Singapore, 2003.
Yu, X-Y, et al., Probing Aqueous Surfaces by TOF-SIMS, Current Trends in Mass Spectrometry, 2011, 34-38.
Yang, L., et al., Probing liquid surfaces under vacuum using SEM and ToF-SIMS, Lab on a Chip, 11, 2011, 2481-2484.
Yang, L., et al., Making a hybrid microfluidic platform compatible for in situ imaging b y vacuum-based techniques, Journal of Vacuum Science and Technology A, 29, 2011, 061101-1-061101-10.
Yang, L., et al., Performance of a microfluidic device for in situ ToF-SIMS analysis of selected organic molecules at aqueous surfaces, Analytical Methods, 5, 2013, 2515-2522.

Hamelin, A., Cyclic voltammetry at gold single-crystal surfaces. Part 1. Behaviour at low-index faces, Journal of Electroanalytical Chemistry, 407, 1996, 1-11.
Hamelin, A., et al., Cyclic voltammetry at gold single-crystal surfaces. Part 2. Behaviour of high-index faces, Journal of Electroanalytical Chemistry, 407, 1996, 13-21.
Ocko, B. M., et al., Structure and Electrocompression of Electrodeposited Iodine Monolayers on Au(111), J. Phys. Chem, 98, 1994, 897-906.
Gao, X. P., et al., Sensitivity of Electrochemical Adlayer Structure to the Metal Crystallographic Orientation: Potential-Dependent Iodide Adsorption on Au(100) in Comparison with Other Low-Index Surfaces, J. Phys. Chem., 98, 1994, 8086-8095.
Itaya, K., In Situ Scanning Tunneling Microscopy in Electrolyte Solutions, Progress in Surface Science, 58, 3, 1998, 121-248.
Tao, N. J., et al., In Situ Scanning Tunneling Microscopy Study of Iodine and Bromine Adsorption on Au(111) under Potential Control, J. Phys. Chem., 96, 1992, 5213-5217.
Lei, H-W, et al., Electrochemical Quartz Crystal Microbalance Study of Halide Adsorption and Concomitant Change of Surface Excess of Water on Highly Ordered Au(111), Langmuir, 13, 1997, 3523-3528.
Hightower, A., et al., A study of iodine adlayers on polycrystalline gold electrodes by in situ electrochemical Rutherford backscattering (ECRBS), Electrochimica Acta, 54, 2009, 1777-1783.
Chen, A., et all, Iodide adsorption at the Au(111) electrode surface, Journal of Electroanalytical Chemistry, 467, 1999, 342-353.
Gu, N., et al. Simultaneous determination of both the calibration constant in an electrochemical quartz crystal microbalance and the active surface area of a polycrystalline gold electrode, Electrochemistry Communications, 2, 2000, 48-50.
Itaya, K., et al., In Situ Scanning Tunneling Microscopy of Organic Molecules Adsorbed on Iodine-Modified Au(111), Ag(111), and Pt(111) Electrodes, Solid-Liquid Electrochemical Interfaces, Amer Chemical Soc, Washington, 665, 11997, 171-188.
McDonald, J. C., et al., Poly(dimethylsiloxane) as a Material for Fabricating Microfluidic Devices, Accounts of Chemical Research, 35, 7, 2002, 491-499.
Yamada, T, et al., Interfacial structure of iodine electrodeposited on Au(111): studies by LEED and in situ STM, Surface Science, 335, 1995, 204-209.
Yamada, T., et al., Structure of Electrochemically Deposited Iodine Adlayer on Au(111) Studied by Ultrahigh-Vacuum Instrumentation and in Situ STM, J. hys. Chem., 99, 1995, 8817-8823.
Batina, N., et al., Atomic Level Characterization of the Iodine-Modified Au(111) Electrode Surface in Perchloric Acid Solution by in-Situ STM and ex-Situ LEED, Langmuir, 11, 1995, 4568-4576.
Ogaki, K., et al., In Situ Scanning Tunneling Microscopy of Underpotential and Bulk Deposition of Silver and Gold (111), Electrochimica Acta, 40, 10, 1995, 124-1257.
Rodriguez, J. F., et al., Determination of the Surface Area of Gold Electrodes by Iodine Chemisorption, J. Electroanal. Chem., 233, 1987, 283-289.
Szakal, C., et al., Surface Sensitivity in Cluster-Ion-Induced Sputtering, Physical Review Letters, 96, 2005, 216104.
Bard, A. J., et al., Studies of the Liquid/Solid Interface by Scanning Tunnelling Microscopy and Scanning Electrochemical Microscopy, Faraday Discuss., 94, 1992, 1-22.
Wang, J., et al., In situ x-ray-diffraction and -reflectivity studies of the Au(111) electrolyte interface: Reconstruction and anion adsorption, Physical Review B, 46, 16, 1992, 10321-10338.
Lee, J., et al., Development of an Automated Digestion and Droplet Deposition Microfluid Chip for Maldi-ToF MS, Journal of Am Soc Mass Spectrom, 19, 2008., 964-972.
Onnerjord, P., et al., Homogeneous Sample Preparation for Automated High Throughput Analysis With Matrix-Assisted Laser Desorption/Ionisation Time-of-Flight Mass Spectrometry, Rapid Communications in Mass Spectrometry, 13, 1999, 315-322.

(56) References Cited

OTHER PUBLICATIONS

Liu, J., et al., Electrophoresis Separation in Open Microchannels, A Method for Coupling Electrophoresis With MALDI-MS Analytica Chemistry, 73, 2001, 2147-2151.

Preisler, J., et al., On-Line MALDI-TOF MS Using a Continuous Deposition Interface, Analytical Chemistry, 70, 24, 1998, 5278-5287.

Murray, K. K., et al., Liquid Sample Introduction for Matrix-Assisted Laser Desorption Ionization, Analytical Chemistry, 65, 18, 1993, 2534-2537.

Orsnes, H., et al., A Rotating Ball Inlet for On-Line MALDI Mass Spectrometry, American Society for Mass Spectrometry, 15, 2004, 1471-1477.

Zhang, X., et al., On-Line Single Droplet Deposition for MALDI Mass Spectrometry, American Society for Mass Spectrometry, 15, 2004, 1471-1477.

Hirschberg, D., et al., Identification of Endothelial Proteins by MALLDI-MS Using a Compact Disc Microfluidic System, The Protein Journal, 23, 4, 2004, 263-271.

\* cited by examiner

MICROFLUIDIC ELECTROCHEMICAL DEVICE AND PROCESS FOR CHEMICAL IMAGING AND ELECTROCHEMICAL ANALYSIS AT THE ELECTRODE-LIQUID INTERFACE IN-SITU

CROSS REFERENCE TO RELATED APPLICATIONS

This application is a Continuation-in-Part of U.S. patent application Ser. No. 13/047,025 filed 14 Mar. 2011 entitled "Systems and Methods for Analyzing Liquids under Vacuum", now issued as U.S. Pat. No. 8,555,710, which reference is incorporated herein in its entirety.

STATEMENT REGARDING RIGHTS TO INVENTION MADE UNDER FEDERALLY-SPONSORED RESEARCH AND DEVELOPMENT

This invention was made with Government support under Contract DE-AC05-76RLO1830 awarded by the U.S. Department of Energy. The Government has certain rights in the invention.

FIELD OF THE INVENTION

The present invention relates generally to electrochemical devices and processes. More particularly, the invention relates to a microfluidic electrochemical device and process for chemical imaging and electrochemical analyses of analytes at the electrode-liquid interface in-situ.

BACKGROUND OF THE INVENTION

The electrode-liquid interface is the most common interface encountered in electrochemical systems and is of great and diverse technological importance. At the molecular level, surface atoms have a different chemical environment than those present in the bulk environment. Thus, a direct observation and fundamental understanding of charge transport, phase transitions, growth of solid interfaces (e.g., adlayers), and reactivity at the electrode-electrolyte interface are needed. The term "adlayer" refers to adsorbed chemical species that form layers on the surface of the electrode and chemically interact with the electrode or substrate. While surface science techniques have made investigation of adsorbed molecules possible, molecular-scale surface science studies are conducted primarily at solid-gas interfaces and solid-vacuum interfaces due to challenges associated with applying surface-sensitive vacuum techniques to high volatility liquids. Consequently, detailed in-situ studies at the electrode-solution interface using surface-sensitive techniques are especially lacking. Ex-situ electrochemical experiments involve removing an electrode from an electrolyte and analyzing sample adlayers present on the electrode in an ambient atmosphere or in an ultra-high vacuum (UHV) instrument or system. However, even well-characterized emersion adlayers may only partially or incompletely represent the real in-situ system. Further, in-situ chemical imaging of actual electrode-electrolyte interfaces has not yet been achieved. Thus, there remains a need for in-situ measurements of electrochemical systems that probe the electrode-liquid sample or liquid interface rather than relying on ex-situ analyses. In addition, new chemical imaging approaches are needed that employ vacuum-based techniques suitable for study of surfaces of high-vapor-pressure liquids and electrode-solution interfaces. The present invention addresses these needs.

SUMMARY OF THE INVENTION

A microfluidic electrochemical device and process are detailed for chemical imaging and electrochemical analysis of analytes at the electrode-liquid sample interface in-situ. The present invention incorporates a microfluidic device for analyzing fluids in a vacuum detailed, e.g., in U.S. patent application Ser. No. 13/047,025 filed 14 Mar. 2011, now allowed. The present invention provides simultaneous multi-modal analyses in concert with combined electrochemical analysis and chemical imaging in real-time or as a function of time that elucidates spatial distributions of various analytes as reactions occur in the liquid sample. The microfluidic electrochemical device may include an electrochemical microfluidic flow chamber (cell) that defines a liquid flow path through the flow chamber. The flow chamber of the microfluidic electrochemical device may be positioned on a silicon substrate such as a silicon wafer or a silicon chip. The electrochemical flow chamber may include one or more inlets and one or more outlets that deliver liquid samples to and from the electrochemical flow chamber, respectively. In some applications, the inlets and the outlets include one or more branches. In some applications, the inlets and the outlets may be positioned apart from another inlet or outlet or include a selected separation distance. The electrochemical flow chamber may include a flow channel with a selected depth. In various applications, the flow chamber may include a flow channel depth between about 0.1 µm and about 1000 µm or greater. In some applications, the flow chamber may include a flow channel depth between about 1 µm and about 1000 µm or greater. The flow chamber may include a support membrane with one or more detection apertures. The support membrane may be constructed of, or include, a material such as silicon nitride (SiN), silicon dioxide ($SiO_2$), including combinations of these various materials.

Probe beams may be delivered from selected analytical instruments through the detection aperture(s) under vacuum into the flow chamber that exposes surfaces of liquid (e.g., liquid) samples including, e.g., liquids, solutions, biological broths, cell growth media containing one or more analytes to the probe beams to provide chemical imaging analysis of analytes at surfaces of liquid samples when the liquid samples are introduced past the detection aperture(s). Surface-sensitive analytical instruments for chemical imaging of liquid sample analytes include, e.g., X-ray photoelectron spectroscopy (XPS); scanning electron microscopy (SEM); transmission electron microscopy (TEM); time-of-flight secondary ion mass spectrometer (ToF-SIMS); helium ion microscopy (HeIM); Auger electron spectroscopy (AES); and Rutherford backscattering spectrometry (RBS). Probe beams from analytical instruments may be introduced into the liquid samples at selected depths, layers, locations, and areas (e.g., within a few microns) to analyze analytes. In various applications, surfaces of liquid samples and working electrode/liquid sample interfaces may be probed with probe beams from selected analytical instrument(s) to selected depths. For example, probe beams from ToF-SIMS instruments may interrogate surfaces to a depth of about 6 nm. However, no depth limitations are intended by the exemplary instrument. In some applications, depth of probe beams may be selected that permit selected regions or layers of the electrode/liquid sample interface to be probed. For example, at selected depths, adsorbed molecules, monolayer films (e.g., 2 Å to 10

Å), diffuse-layers (1 nm to 1 μm), and/or modified films (e.g., 1 nm to 1 μm) may be investigated.

The microfluidic electrochemical device may also include electrodes such a working electrode, a counter electrode, and/or a reference electrode. Electrodes provide electrochemical analyses of analytes in liquid samples, e.g., in concert with cyclic voltammetry (CV). Electrodes in the microfluidic electrochemical device may be in the form of wires, thin films, and sputter-deposited thin films. Electrodes may be constructed of, or include, metals, metal oxides, carbon, graphene, or other suitable electrode materials including combinations of these various materials. In some applications, the working electrode and the counter electrode may be integrated with a reference electrode on a single substrate. In some applications, the counter electrode and the reference electrode may be positioned on a substrate that is different from the substrate that contains the working electrode. In some applications, the working electrode may be positioned above the flow channel within the flow chamber of the electrochemical device and positioned beneath the detection aperture (window). The counter electrode and the reference electrode may be disposed below the flow channel in the flow chamber. The working electrode may be configured to apply a selected potential into the sample between the working electrode and the reference electrode to drive reactions in the liquid sample as a function of time, space, and/or potential. The counter electrode may be configured to measure electrical current stemming from reactions involving analytes in the liquid sample at the surface of the working electrode. The microfluidic electrochemical device is configured to provide electrochemical analysis and chemical imaging of analytes at surfaces of the liquid sample and at the working electrode-liquid interface in-situ individually or simultaneously at selected depths or selected layers. Electrodes in the microfluidic electrochemical device may be coupled to an external workstation that is configured to deliver potentials between the working electrode and reference electrode and to measure current between the working electrode and the counter electrode.

The present invention also includes a process for simultaneous electrochemical analysis and chemical imaging of analytes present in samples of various types. The process may include introducing a liquid sample containing one or more analytes through a liquid flow path in the microfluidic flow chamber of a microfluidic electrochemical device. Selected potentials may be delivered between a working electrode and a reference electrode in the microfluidic flow chamber to drive reactions of the one or more analytes in the liquid sample as a function of time, space, and/or potential. The sample in the liquid flow path may be exposed to one or more probe beams from selected analytical instruments under vacuum to provide chemical imaging of analytes at a selected depth or a selected layer of a liquid sample or at the working electrode-liquid sample interface in-situ.

In some applications, the method may provide simultaneous chemical imaging and electrochemical analyses of analytes including chemical and molecular species present at the working electrode-liquid sample interface in-situ including selected locations, depths, layers, and surfaces thereof.

Electrochemical analysis may be provided, e.g., by cyclic voltammetry. Chemical imaging may be provided in concert with an analytical method including, but not limited to, e.g., X-ray photoelectron spectroscopy (XPS); scanning electron microscopy (SEM); secondary ion mass spectrometry (SIMS); helium ion microscopy (HelM); Auger electron spectroscopy (AES); Rutherford backscattering spectrometry (RBS); transmission electron microscopy (TEM), and combinations of these various methods.

Electrical current between the working electrode and a counter electrode may be measured to provide electrochemical analysis of various chemical and molecular species stemming from reactions involving various analytes. Various potentials may be delivered from an electrochemical workstation positioned external to the microfluidic electrochemical device. Current may be measured by the same electrochemical workstation. In some applications, the liquid sample may include an electrolyte. In some applications, the sample may be a buffer solution or include a buffer. In some applications, the sample may be a biological sample containing one or more biological analytes selected from: cells, bacteria, other biological components, and combinations of these various biological analytes.

In some applications, chemical imaging and electrochemical analysis may include determining chemical species at the surface of the working electrode-liquid sample interface in-situ. In some applications, chemical imaging may include imaging adsorbed molecules at the surface of the working electrode and in solutions adjacent the working electrode in-situ. In some applications, the method may include observing or tracking compositional changes of an electrolyte as a function of time in-situ. In some applications, the method may include a time-resolved and/or a space-resolved determination of reaction products and intermediate chemical species as electron transfer occurs in the sample in-situ. In some applications, the method may include electrochemically determining and chemically imaging material changes to an electrode in a microfluidic electrochemical device as potential is varied.

The purpose of the foregoing abstract is to enable the United States Patent and Trademark Office and the public generally, especially scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way. A more complete appreciation of the invention will be readily obtained by reference to the following description of the accompanying drawings in which like numerals in different figures represent the same structures or elements.

DETAILED DESCRIPTION

A new microfluidic electrochemical device and process are detailed that provide combined chemical imaging and electrochemical analysis of analytes at the electrode-solution interface in-situ. Chemical imaging is described herein in concert with one exemplary surface sensitive instrument, i.e., a ToF-SIMS. However, the invention is not limited thereto, as detailed further herein. The following description includes a best mode of the present invention. Various advantages and novel features of the present invention are described herein and will become further readily apparent to those skilled in this art from the following detailed description. As will be realized, the invention is capable of modification in various respects without departing from the invention. It should be understood that there is no intention to limit the invention to the specific forms disclosed, but, on the contrary, the invention covers all modifications, alternative constructions, and equivalents falling within the spirit and scope of the invention as defined in the claims. Accordingly, the drawings and description of the preferred embodiment set forth hereafter are to be regarded as illustrative in nature, and not as restrictive.

Figure 1:
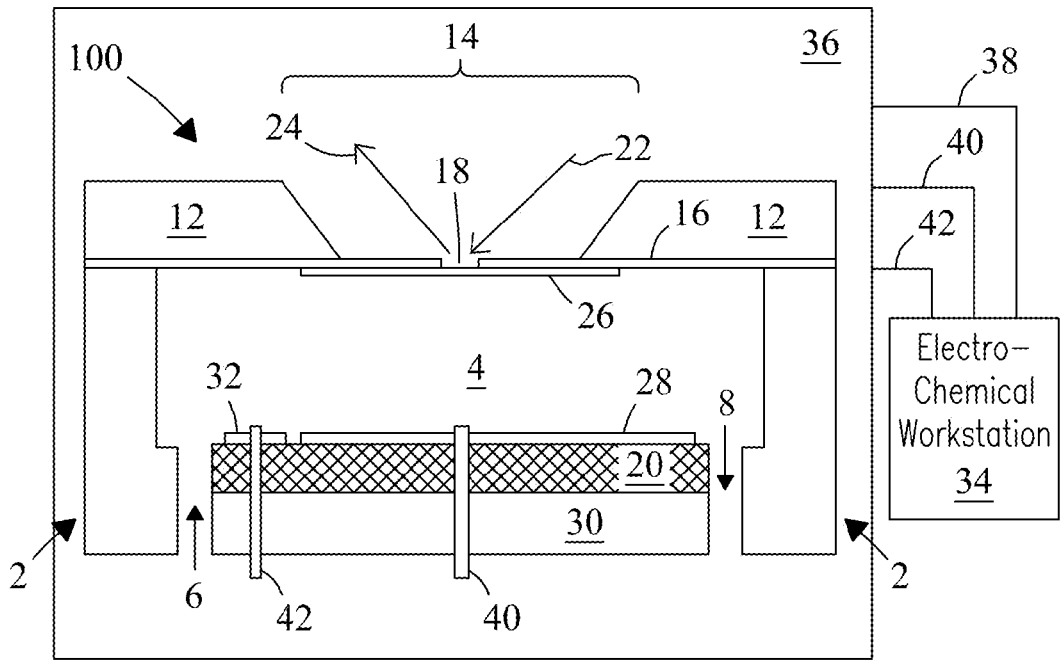
FIG. 1 illustrates a side view of a microfluidic electrochemical device of the present invention.

FIG. 1 is a schematic showing a side view of a microfluidic electrochemical device 100 of the present invention for combined chemical imaging and electrochemical analysis of analytes at the electrode-liquid sample interface in-situ. Electrochemical device 100 may include a microfluidic electrochemical flow chamber (cell) 2 with a microfluidic flow channel 4, one or more fluid inlets 6, and one or more fluid outlets 8. The term "microfluidic" refers to the depth of flow channel 4 in electrochemical flow chamber 2. Flow channel 4 may include a depth that varies depending on the selected application. In some embodiments, flow channel 4 may include a depth dimension greater than or equal to about 10 micrometers (μm). In some embodiments, flow channel 4 may include a depth dimension between about 10 micrometers (μm) and about 300 micrometers (μm). In some embodiments, flow channel 4 may include a depth dimension at or below 300 micrometers (μm). In the exemplary embodiment, flow channel 4 may include selected dimensions: 2.5 mm (L)×2.5 mm (W)×0.3 mm (H).

One or more fluid reservoirs (not shown) may be positioned, e.g., below flow chamber 2 at respective ends of inlets 6 and outlets 8 to contain samples that are flowed into and out of flow chamber 2. In some embodiments, fluid reservoirs may include a fluid volume or capacity of approximately 20 μL, but volumes are not limited. Flow channel 4 can connect fluid inlets 6 to fluid outlets 8 to enclose the circulation loop. Both static and dynamic flow modes may be employed. Various liquids and liquid samples may be circulated through flow chamber (cell) 2 to conduct chemical imaging and electrochemical analysis. In some embodiments, an external syringe pump (described further herein) may be used to introduce selected samples into microfluidic chamber 2. In some embodiments, samples may be introduced through flow chamber 2 at a flow rate below 4 μL per min (i.e., 4 μL/min). However, flow rates are not limited.

Electrochemical flow chamber (cell) 2 may include a top frame 12 constructed of, e.g., a semiconductor wafer composed of a suitable frame material such as silicon (Si), silicon nitride (SiN), silicon dioxide ($SiO_2$), and combinations of these materials. Top frame 12 may include a selected thickness. In some embodiments, top frame 12 may include a thickness dimension of between about 100 μm and about 500 μm. In some embodiments, top frame 10 may include dimensions of 7.5 mm (W)×7.5 mm (L) for a coverage area of about 56.3 $mm^2$, but dimensions are not intended to be limited.

Top frame 12 may include a detection area 14 that is open to atmosphere and may include selected shapes. In the figure, detection area 14 is in the form of a V-shaped well positioned, e.g., through the center of top frame 12, but position and shape are not limited.

Top frame 12 may include a support membrane 16 constructed of a suitable support material such as SiN, $SiO_2$, Si, or another electron transparent material. In various embodiments, support membrane 16 may include a thickness dimension of between about 25 nm and about 200 nm. Thickness depends in part on dimensions of other structural components of electrochemical flow chamber 2. For example, support membrane 16 may include a greater thickness when top frame 12 has a greater surface area to provide suitable support. Thus, dimensions are not intended to be limited.

Support membrane 16 may be bonded to the top of microfluidic flow chamber 2 to enclose flow chamber 2. Bonding between top frame 12 (e.g., Si wafer) and the top of microfluidic flow chamber 2 may be accomplished, e.g., with an oxygen plasma, or another suitable bonding method that provides a leak-tight fluid seal in flow chamber 2.

Support membrane 16 (e.g., SiN membrane 16) may be positioned, e.g., immediately below top frame 12 (e.g., Si frame 12) below detection area 14. Support membrane 16 may include one or more detection apertures (windows) 18 that open into microfluidic flow chamber 2 to allow entry of one or more probe beams 22 from selected surface-sensitive analytical instruments (e.g., ToF-SIMS) into samples and solutions introduced to electrochemical flow chamber 2 to provide chemical imaging of analytes present in the samples. Detection apertures (windows) 18 may also be positioned at various locations on support membrane 16, e.g., above flow channel 4. Detection apertures (windows) 18 may be bored through support membrane 16 using, e.g., a primary ion beam from a ToF-SIMS instrument or a focused ion beam from an SEM instrument or other focused energy beams. Detection apertures 18 into electrochemical flow chamber 2 may be of any size that permits entry of probe beams 22 from selected analytical instruments that probe liquid samples and returns analyte ions in a secondary beam 24 back to the analytical instruments for determination or analysis. Detection apertures (windows) 18 have a size sufficiently small to minimize mean-free path length to minimize fluid loss from microfluidic flow chamber 2 and to maximize successful collisions between probe beams 22 and analytes of interest when probe beams 22 are introduced into samples including, e.g., solutions and battery electrolytes. In some embodiments, detection apertures 18 may include a size less than about 3 microns (μm). In the exemplary embodiment, detection apertures 18 may include a size of about 2 μm. In some embodiments, detection apertures 18 may include a size less than about 1 micron (μm).

Prior to assembly, microfluidic electrochemical flow chamber 2 (e.g., not yet including top frame 12 and support membrane 16) may be sputter-coated with a thin (e.g., about 10 nm to about 30 nm) layer of gold that seals pores of the elastomer on the exterior surface of flow chamber 2 to retain samples and liquids or other fluids when introduced to flow chamber 2.

Electrochemical flow chamber 2 may include up to three electrodes configured to perform electrochemical analyses of analytes in liquid samples or solutions introduced to electrochemical device 100. Electrodes may include a working electrode 26, a counter electrode 28, and a reference electrode 32 that each couple to an external electrochemical workstation 34. Electrodes 26, 28, and 32 may be constructed of selected metals including, e.g., gold (Au), platinum (Pt) and copper (Cu); metal oxides including, e.g., CuO, CoO, and $V_2O_5$; and carbon (C) such as graphene. In the instant embodiment, working electrode 26 may be constructed of gold (Au) or another suitable electrode material. Counter electrode 28 and reference electrode 32 may be constructed of selected metals such as platinum (Pt) metal or another suitable electrode material.

In the instant embodiment, working electrode 26 may be positioned on an underside of support membrane 16 at a top end of microfluidic flow chamber 2 below detection aperture 18 above flow channel 4. A metal connecting wire 38 composed of copper or another suitable conducting material of a selected length may couple (not shown) to working electrode 26 inside flow chamber 2. Another end of conducting metal wire 38 may exit, e.g., through a side of flow chamber 2 and couple working electrode 26 to an electrochemical work station 34 (e.g., Model 824 Electrochemical Detector, CH Instruments, Inc., Austin, Tex., USA) positioned external to flow chamber 2. Counter electrode 28 and reference electrode 32 may be positioned at a bottom end of microfluidic flow chamber 2 atop a mounting block 20 positioned below flow channel 4. Mounting block 20 may be positioned, e.g., atop an elastomer block 30 detailed further herein.

Working electrode 26 may deliver a selected potential (E) into a sample (e.g., solution, electrolyte, biofilm, or other sample) between working electrode 26 and reference electrode 32 to drive reactions of various analytes in the sample as a function of time, space, and/or potential. Reference electrode 32 provides a fixed electrode potential from which other reaction potentials may be calibrated or otherwise calculated. Counter electrode 28 may measure electrical current stemming from reactions occurring between the various analytes in the liquid sample. Electrodes 26, 28, and 32 in combination provide electrochemical analysis of analytes in the liquid sample, e.g., at the working electrode-sample interface in-situ.

Electrochemical device 100 is configured to sustain a high vacuum condition, e.g., achieving pressures less than about $5 \times 10^{-7}$ Torr when introduced into vacuum chamber 36 of a selected analytical instrument (e.g., ToF-SIMS, SEM) during operation. Electrochemical device 100 may be used one or more or multiple times by introducing different liquid samples including solutions and battery electrolytes into electrochemical chamber (cell) 2 at various or selected conditions including, e.g., ambient conditions or high vacuum conditions. Electrochemical device 100 may be discarded when performance warrants a replacement device.

Lab-on-a Chip

In some embodiments, microfluidic electrochemical device 100 may be fabricated as a lab-on-a-chip device. Referring back to FIG. 1, a negative mold or template (not shown) may be used for casting microfluidic electrochemical chamber (cell) 2 and associated internal features including, e.g., flow channel 4, inlets 6, and outlets 8 each with their selected dimensions. Negative molds may be fabricated on a flat silicon chip or wafer, e.g., as detailed by Yu et al. (e.g., in "Microfluid Nanofluid", DOI 10.1007/10404-013-1199-4), which reference is incorporated herein in its entirety. In the exemplary embodiment, the negative mold was fabricated on silicon (Si) substrate 12. Internal features were constructed using a selected photoresist material (e.g., SU-8 photoresist, Microchem, Newton, Mass., USA) placed onto a Si wafer substrate 12. The photoresist may be spun or spread at a selected thickness over the silicon substrate 12. A photomask with a pattern selected to provide the internal features of microfluidic flow chamber 2 may be designed using design software (e.g., AutoCAD) and then printed with a mask printer (e.g., Model SF-100 Xpress mask printer, Intelligent Micro Patterning LLC, St. Petersburg, Fla., USA). The photomask when placed onto Si substrate 12 and exposed to UV light transfers the desired pattern onto the photoresist and solidifies the photoresist, creating the reverse mold on the Si substrate 12. The pattern permits casting of microfluidic electrochemical flow chamber (cell) 2 using a selected elastomer that achieves desired high aspect ratio features and internal (microchannel) flow structures.

In some embodiments, microfluidic electrochemical flow chamber (cell) 2 may be constructed of an elastomer such as, e.g., polydimethylsiloxane (PDMS). PDMS elastomer may be mixed as a prepolymer with a curing agent (e.g., Sylgard 184, Dow Corning Co., Midland, Mich., USA), degassed under vacuum (e.g., 30 minutes in a vacuum dessicator), and poured onto the reverse template (mold) (not shown) located on Si substrate 12 containing selected high aspect ratio features (e.g., fluid channels) at a selected thickness (e.g., 1 cm), and then cured in an oven for a selected time (e.g., ~1 hour) at a selected temperature (e.g., 70° C. to 75° C.). Cured PDMS may be removed from the template mold and cut to a selected size (~12 mm×12 mm) to form microfluidic electrochemical flow chamber (cell) 2 with its microfluidic features including a flow channel 4, one or more fluid (microchannel) inlets 6, and one or more fluid (microchannel) outlets 8 each with selected and/or respective channel dimensions detailed herein. In some embodiments, flow channel 4 may include a depth of about 300 μm, but depth is not intended to be limited. In some embodiments, inlet channels 6 and outlet channels 8 may include dimensions of, e.g., 100 μm (L)×100 μm (W) by 200 μm (depth).

Microfluidic electrochemical flow chamber (cell) 2 may include a base elastomer block 30 upon which an electrode mounting block 20 may be positioned. Electrode mounting block 20 may be constructed, e.g., of elastomers, hard plastics, glass, silicon, including combinations of these various materials. In some embodiments, electrode mounting block 20 may be constructed of a high-temperature epoxy (e.g., Duralco 4461 epoxy, Cotronics Co., Brooklyn, N.Y., USA). Electrode mounting block 20 may be formed by introducing the epoxy mixture containing a curing agent in a template patterned with SU-8 as described previously for PDMS microfluidic chamber 2. No limitations are intended.

In some embodiments, metal connecting wires 40 and 42 composed of copper or another suitable conducting material of a selected length may be introduced (e.g., inserted) through two through-holes (e.g., ~0.5 mm diameter) (not shown) introduced e.g., with a syringe needle (e.g., a Model No.: NE-301PL-C syringe needle, Small Parts, Inc., Miramar, Fla., USA) through a bottom end of microfluidic flow chamber 2. One end of connecting wires 40 and 42 introduced through the bottom end of chamber 2 may be coupled respectively to counter electrode 28 (e.g., 600 μm diameter) and to reference electrode 32 (e.g., 350 μm diameter) supported on electrode mounting block 20. Another end of conducting metal wires 40 and 42 may exit flow chamber (cell) 2 e.g., from the bottom end to couple counter electrode 28 and reference electrode 32 to external electrochemical work station 34. Work station 34 may deliver selected potentials to electrodes 26, 28, and 32 of electrochemical device 100.

In some embodiments, an epoxy mixture containing curing agent may be introduced (e.g., poured) over the top of conducting metal wires 40 and 42 introduced through the bottom end of microfluidic flow chamber 2 to a height that leaves a top end of conducting metal wires 40 and 42 exposed for subsequent coupling to counter electrode 26 and reference electrode 32, respectively. The epoxy mixture may be cured for a selected time (e.g., 24 hours) at a selected temperature (e.g., room temperature) to embed conducting metal wires 40 and 42 in the epoxy of electrode mounting block 20. Cured epoxy in electrode mounting block 20 may be subsequently heated in an oven for a selected time (e.g., 2 hours) at a selected temperature (e.g., 110° C.) to anneal assembled device components. With conducting wires 40 and 42 embedded in electrode mounting block 20, surface of electrode mounting block 20 may be polished, e.g., with fine sand papers or other polishing materials to provide a flat surface upon which counter electrode 26 and reference electrode 32 may be constructed. Counter electrode 26 and reference electrode 32 may be constructed, e.g., by sputter-coating the desired metal electrode material [e.g., platinum (Pt)] onto the surface of the mounting block 20 and then coupling counter electrode 26 and reference electrode 32 to connecting wires 40 and 42, respectively. Wires 40 and 42 when coupled to counter electrode 26 and reference electrode 32 in electrode mounting block 20 may then be connected to the electrochemical workstation (FIG. 1) located external to electrochemical device 100.

Figure 2A:
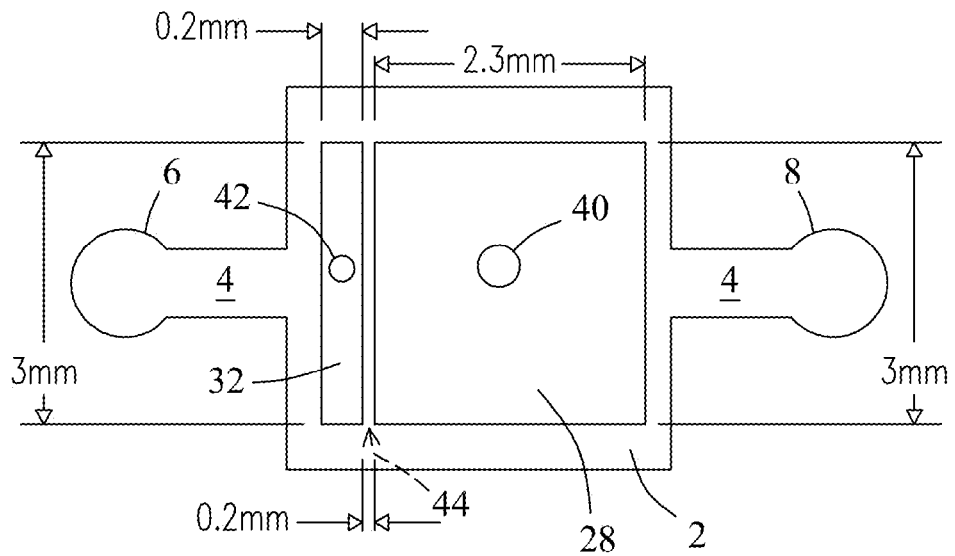
FIGS. 2a-2d show different electrode configurations for the present invention.

FIG. 2a shows a top perspective view of an exemplary electrode configuration of the present invention of a thin-film design. In the instant embodiment, counter electrode 28 and reference electrode 32 may be thin film electrodes constructed of platinum (Pt) or another suitable electrode material. As described previously herein, electrodes 28 and 32 may be sputter-deposited electrodes (Denton Vacuum, LLC, Moorestown, N.J.). As shown in the figure, counter electrode 28 may be separated from reference electrode 32 prior to sputtering with, e.g., a narrow [e.g., 3 mm (L)×0.2 mm (W)] strip of insulating tape 44 or other insulating material. The platinum (Pt) target (Kurt J. Lesker Co., Clariton, Pa., USA) may include a purity of, e.g., 99.99% or better. Insulating tape 44 may be removed after sputter coating to yield a counter electrode 28 that is physically separated from reference electrode 32. Counter electrode 28 and reference electrode 32 may be positioned at a bottom end of electrochemical flow chamber 2 on top of the electrode mounting block (FIG. 1) below the working electrode (FIG. 1). In the instant embodiment, counter electrode 28 may include exemplary dimensions of, e.g., 3 mm (L)×2.3 mm (W). Reference electrode 32 may include exemplary dimensions of, e.g., 3 mm (L)×0.5 mm (W). In some embodiments, counter electrode 28 and reference electrode 32 may include a thickness dimension of about 200 nm, but dimensions are not limited. Connection wires 40 and 42 may respectively couple counter electrode 28 and reference electrode 32 to electrochemical workstation (FIG. 1) positioned external to electrochemical device 100. As shown in the figure, electrochemical flow chamber 2 may include a single inlet 6 for introducing samples (e.g., electrolytes, biological fluids including, e.g., cell growth media, and other solutions), and a single outlet 8 for removing samples from electrochemical flow chamber 2.

Figure 2B:
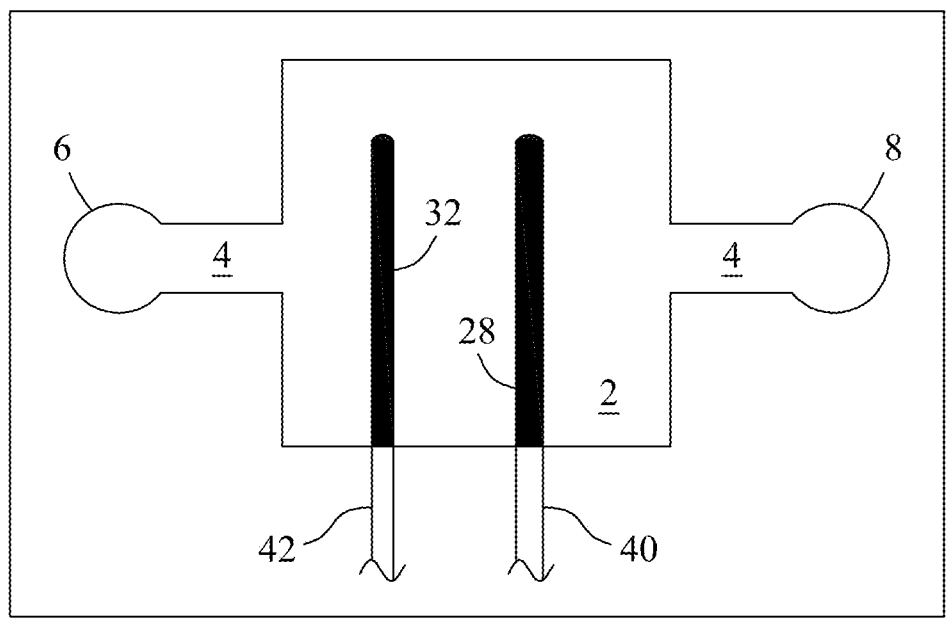

FIG. 2b shows a top perspective view of another exemplary electrode configuration of the present invention of a wire electrode design. In the figure, counter electrode 28 and reference electrode 32 may be metal microwires constructed of selected metals such as platinum (Pt) or other conducting metals. Wires 28 and 32 may each be seated in a microchannel (not shown) that fits the dimensions of the wires on the face of the electrode mounting block (FIG. 1) within electrochemical flow chamber 2. Counter electrode microwire 28 may be separated from reference electrode microwire 32. In various embodiments, counter electrode microwire 28 and reference electrode microwire 32 may include an outer diameter of from about 25 μm to about 500 μm. In the instant embodiment, connection wires 40 and 42 that couple to wire electrodes 28 and 32 may exit through a side of electrochemical flow chamber 2 and connect with an electrochemical workstation (FIG. 1) located external to electrochemical flow chamber (FIG. 1). However, insertion location for coupling wires is not limited. In the instant embodiment, electrochemical flow chamber 2 may include a single inlet 6 for introducing samples and a single outlet 8 for removing samples from electrochemical flow chamber 2.

Figure 2C:
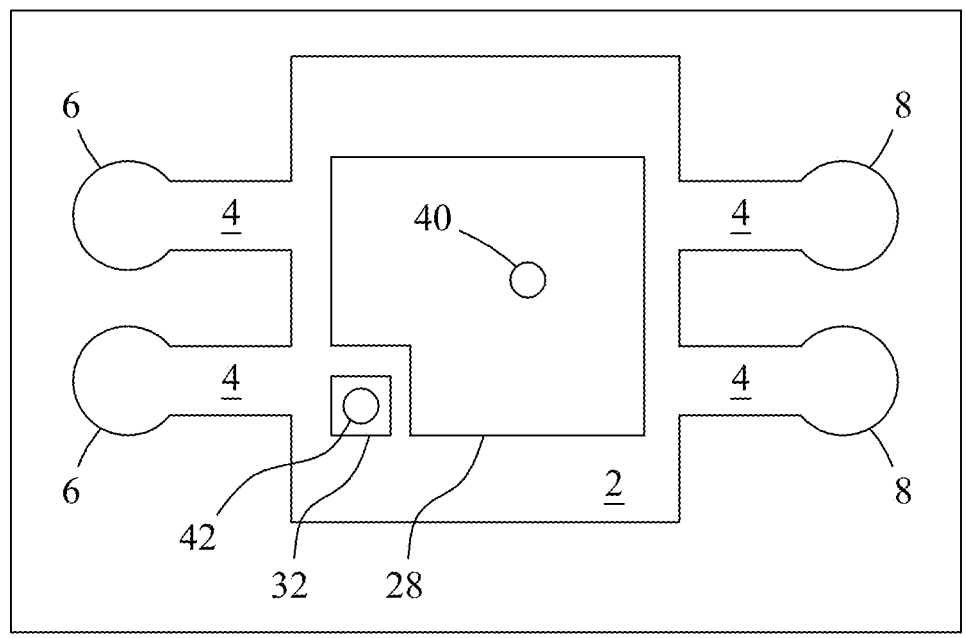

FIG. 2c shows a top perspective view of another exemplary electrode configuration of the present invention. In this embodiment, electrode mounting block 20 may be positioned at the bottom of electrochemical flow chamber 2 below the working electrode (FIG. 1). Counter electrode 28 and reference electrode 32 may be sputter-deposited thin film electrodes (Denton Vacuum, LLC, Moorestown, N.J.) constructed of platinum (Pt) or another suitable electrode material. In some embodiments, counter electrode 28 and reference electrode 32 may include an exemplary thickness of, e.g., 200 nm, but thickness is not limited. Dimensions of counter electrode 28 and reference electrode 32 may be tailored to fit dimensions of the electrode mounting block (FIG. 1). In the figure, reference electrode 32 may be electrically separate from counter electrode 28. In some embodiments, counter electrode 28 may span a surface area on the top of electrode mounting block (FIG. 1) greater than about 60%. Reference electrode 32 may occupy a corner of the electrode mounting block and include a surface area of less than about 40%. However, coverage areas are not limited. Connection wires 40 and 42 from an electrochemical workstation (FIG. 1) located external to electrochemical flow chamber 2 may be introduced, e.g., through the bottom of electrochemical flow chamber 2 and coupled, e.g., at the center of counter electrode 28 and reference electrode 32, respectively. In the instant embodiment, electrochemical flow chamber 2 may include multiple (e.g., two or more) inlets 6 for introducing samples and different liquids into flow chamber 2 and multiple (e.g., two or more) outlets 8 for removing samples and liquids from electrochemical flow chamber 2. As shown in the figure, each inlet may be separate from another inlet and each outlet may be separate from another outlet.

Figure 2D:
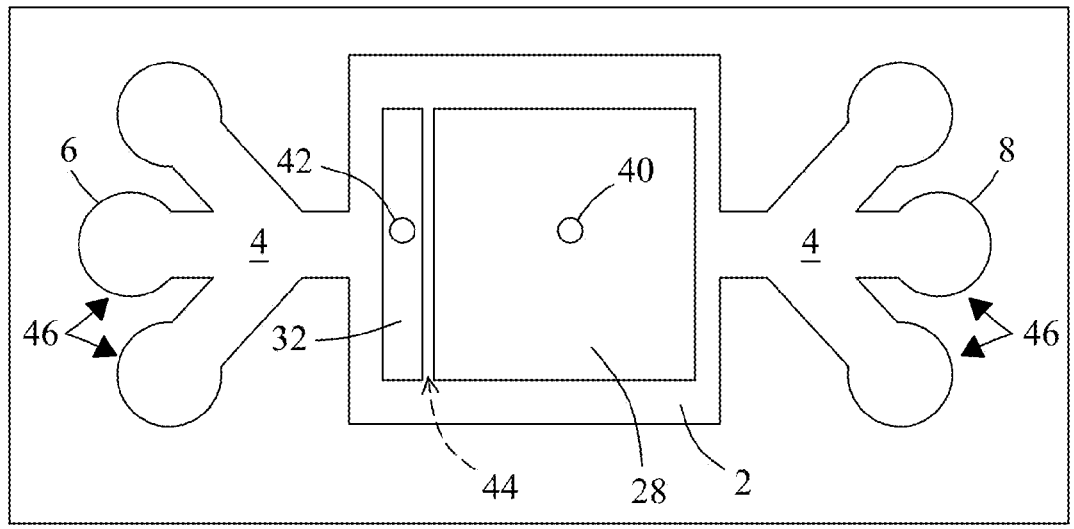

FIG. 2d shows a top perspective view of another exemplary electrode configuration of the present invention. In the instant embodiment, counter electrode 28 and reference electrode 32 may be thin film electrodes constructed of platinum (Pt) or another suitable electrode material. Counter electrode 28 and reference electrode 32 may be sputter-deposited electrodes (Denton Vacuum, LLC, Moorestown, N.J.). Counter electrode 28 may be separated from reference electrode 32 prior to sputtering with, e.g., a narrow [e.g., 3 mm (L)×0.2 mm (W)] strip of insulating tape 44 (Electro Tape Specialities, Inc., FL, USA) or another insulating material. The platinum (Pt) target (Kurt J. Lesker Co., Clariton, Pa., USA) may include a selected purity of, e.g., 99.99%. Insulating tape 44 may be removed after sputter coating to yield a counter electrode 28 that is physically separated from reference electrode 32. Sputter-deposited platinum (Pt) counter electrode 28 and reference electrode 32 may include an exemplary thickness of, e.g., 200 nm. Counter electrode 28 may include an exemplary length (L) of about 3 mm and an exemplary width (W) of about 2.3 mm, but dimensions are not limited thereto. Reference electrode 32 may include an exemplary length (L) of about 3 mm width and an exemplary (W) of about 0.5 mm. However, dimensions are not intended to be limited. Connection wires 40 and 42 from an electrochemical workstation (FIG. 1) located external to electrochemical flow chamber 2 may be introduced, e.g., through the bottom of electrochemical flow chamber 2 and coupled, e.g., at the center of counter electrode 28 and reference electrode 32, respectively. In the instant embodiment, electrochemical flow chamber 2 may include a patterned inlet 6 with multiple (e.g., three) branches 46 that permit mixing of various samples, liquids, solutions, or battery electrolytes introduced into flow chamber 2 and a patterned outlet 8 with multiple (e.g., two) branches 46 for retrieving various samples, liquids, solutions, or battery electrolytes from electrochemical flow chamber 2. Number of branches 46 is not limited.

Figure 3A:
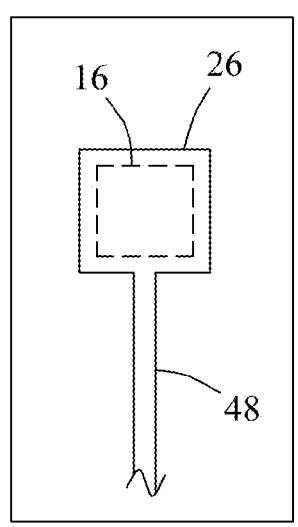
FIGS. 3a-3b show two exemplary gold electrode designs for the present invention.

FIG. 3a shows an exemplary working electrode 26 of a single electrode design that may be positioned on the underside of silicon nitride (SiN) membrane 16. In the exemplary design, working electrode 26 may be composed of a thin film of polycrystalline gold (Au) or another suitable electrode material sputter-deposited onto the underside of SiN support membrane 16 using selected coating targets (e.g., Model 30800 series targets, Ladd Research Industries Inc., Burlington, Vt., USA). In the instant design, SiN membrane 16 positioned above working electrode 26 may include a length (L) dimension of, e.g., 1.5 mm and a width (W) dimension of, e.g., 1.5 mm (W) for a surface area of 2.25 $mm^2$. Herein, the electrode surface area may be presumed to be equal to the geometric area. In the instant design, working electrode 26 may include a length (L) dimension of, e.g., 2 mm and a width (W) dimension of, e.g., 2 mm for a total working area of about 4.0 $mm^2$. However, areas are not intended to be limited. Working electrode 26 may couple to a conducting metal connector 48 (e.g., a strip connector), e.g., constructed of sputter-deposited gold (Au) or another suitable conducting material that serves as a conductive couple between working electrode 26 and the external workstation (FIG. 1).

Figure 3B:
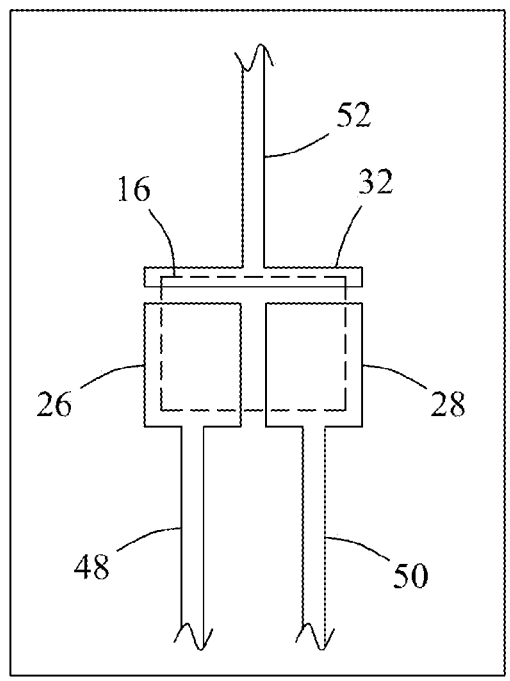

FIG. 3b shows another electrode configuration of the present invention of an integrated electrode design. In the instant embodiment, working electrode 26 is integrated with a counter electrode 28 and a reference electrode 32, with all electrodes positioned beneath the silicon nitride (SiN) support membrane 16. As shown in the figure, electrodes 26, 28, and 32 are all electrically separated. Each electrode 26, 28, and 32 may further couple to respective metal connectors (e.g., a strip connector) 48, 50, and 52 constructed of sputter-deposited gold (Au) or another suitable metal or conducting material. Strip connectors 48, 50, and 52 serve as conductive couples between each electrode and the external workstation (FIG. 1).

Figure 4:
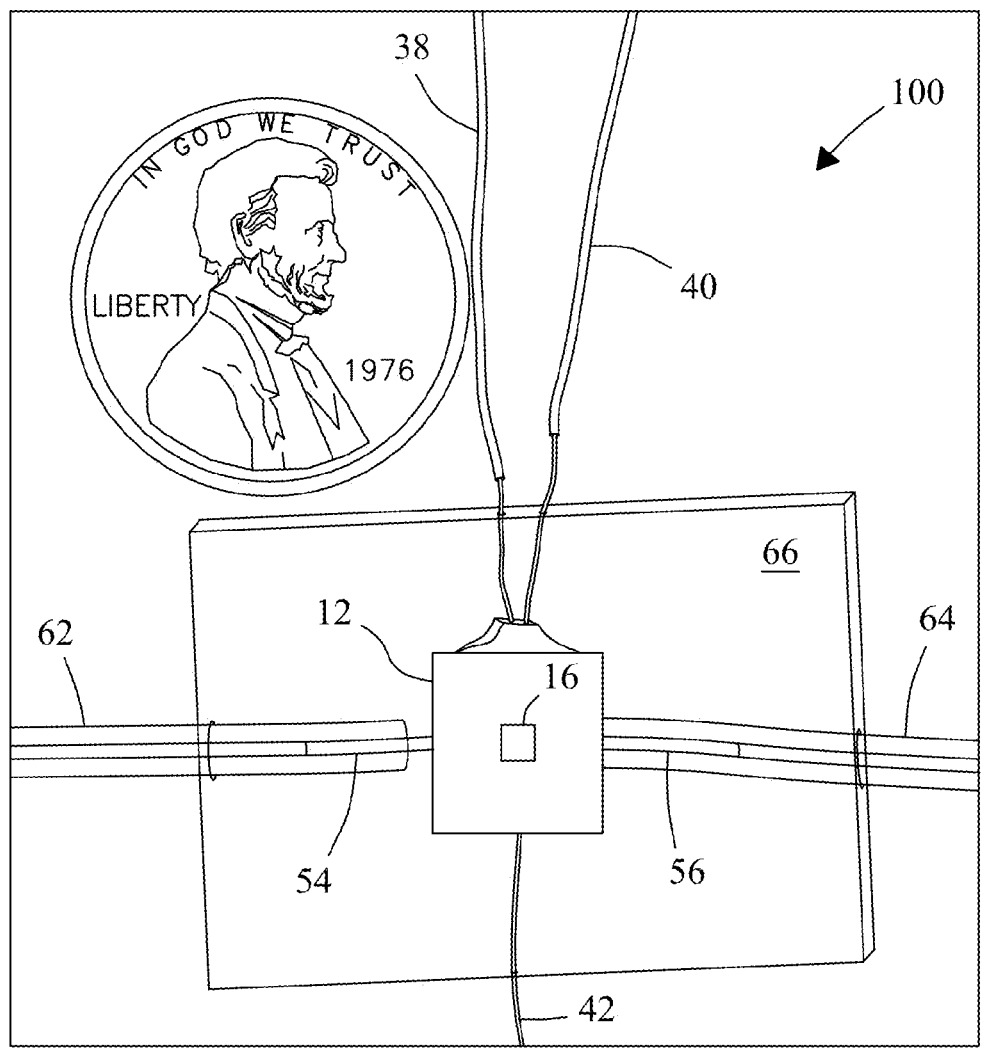
FIG. 4 is a photograph showing the microfluidic electrochemical device of the present invention.

FIG. 4 illustrates a top perspective view of the assembled electrochemical device 100. Device 100 includes a working electrode, counter electrode, and reference electrode (not shown) in an integrated electrode design described previously in reference to FIG. 3b. In the instant design, working electrode, counter electrode, and reference electrode may be sputter-deposited polycrystalline gold films positioned beneath SiN membrane 16 below top silicon frame 12. Each electrode couples to an external workstation (FIG. 1) via respective metal wires 38, 40, and 42. In the instant embodiment, metal flow tube 54 may connect to a fluid inlet (FIG. 1). Metal flow tube 56 may couple to a fluid outlet (FIG. 1) within electrochemical device 100. Metal flow tubes 54 and 56 may include an outer diameter of, e.g., 0.025 inches (0.064 mm), an inner diameter of 0.017 inches (0.043 mm), and a length of about 0.5 inches (12.7 mm). Metal flow tubes 54 and 56 may further couple to flexible flow tubing 62 and 64 (e.g., TEFLON® flow tubing, VICI Valco Instruments, Tex., USA) that provide a flow of liquid samples including solutions and electrolytes through flow chamber (FIG. 1). Flexible flow tubing 62 and 64 may include an outer diameter (O.D.) of, e.g., 0.025 inches (0.064 mm), but dimensions are not limited. Top silicon frame 12, SiN membrane 16, metal coupling tubes 54 and 56 and flexible flow tubing 62 and 64 may be encased in a PDMS enclosure (block) 66. PDMS enclosure 66 may be constructed in a mold (not shown) following assembly of electrochemical flow device 100.

Chemical Imaging

Chemical imaging performed in concert with various probe instruments generates images of chemical analytes in liquid samples of interest over a selected sampling area. Data provide spectral, spatial, and/or temporal information across different time and space scales depending on the various sampling probes used to collect the data. Chemical imaging may be performed in concert with one or more vacuum-based, surface-sensitive chemical analysis (analytical probe) instruments including, but not limited to, e.g., X-ray photoelectron spectroscopy (XPS); scanning electron microscopy (SEM); secondary ion mass spectrometry (SIMS); time-of-flight secondary ion mass spectrometry (ToF-SIMS); helium ion microscopy (HeIM); Auger electron spectroscopy (AES); Rutherford backscattering spectrometry (RBS); and transmission electron microscopy (TEM). The probe instrument analyzes the surface of the sample by introducing a probe beam through the detection aperture (FIG. 1) into the liquid sample at a selected depth. For example, surfaces of liquid samples and surfaces at the working electrode/liquid sample interfaces may be probed with probe beams delivered from selected analytical instruments at selected depths. In various embodiments, probe beams may probe various depths of liquid samples. In some embodiments, depth may be selected up to about 6 nm that permits selected regions or layers of the electrode/liquid sample interface to be probed. For example, at selected depths, adsorbed molecules, monolayer films (e.g., 2 Å to 10 Å), diffuse-layers (1 nm to 1 μm), and/or modified films (e.g., 1 nm to 1 μm) may be investigated. All depths as will be selected by those of ordinary skill in the art in view of the disclosure are within the scope of the present invention. No limitations are intended.

A liquid sample or interface may be analyzed and data collected at a first location or surface that provides a first spectral map. Each pixel of the image map may correspond to a m/z spectrum at that pixel location. The sampling probe may then analyze a second location or surface of the liquid sample within the sampling area that provides a second spectral map. The process may be repeated until a preselected, and statistically significant, sampling frequency is obtained. Signal intensities from the collection of mass spectra on the sampling surface may be plotted as a function of voltage or scanning depth, which allows a spatial profile or map to be generated of different chemical species identified within the sampling area for a given sample).

Figure 5:
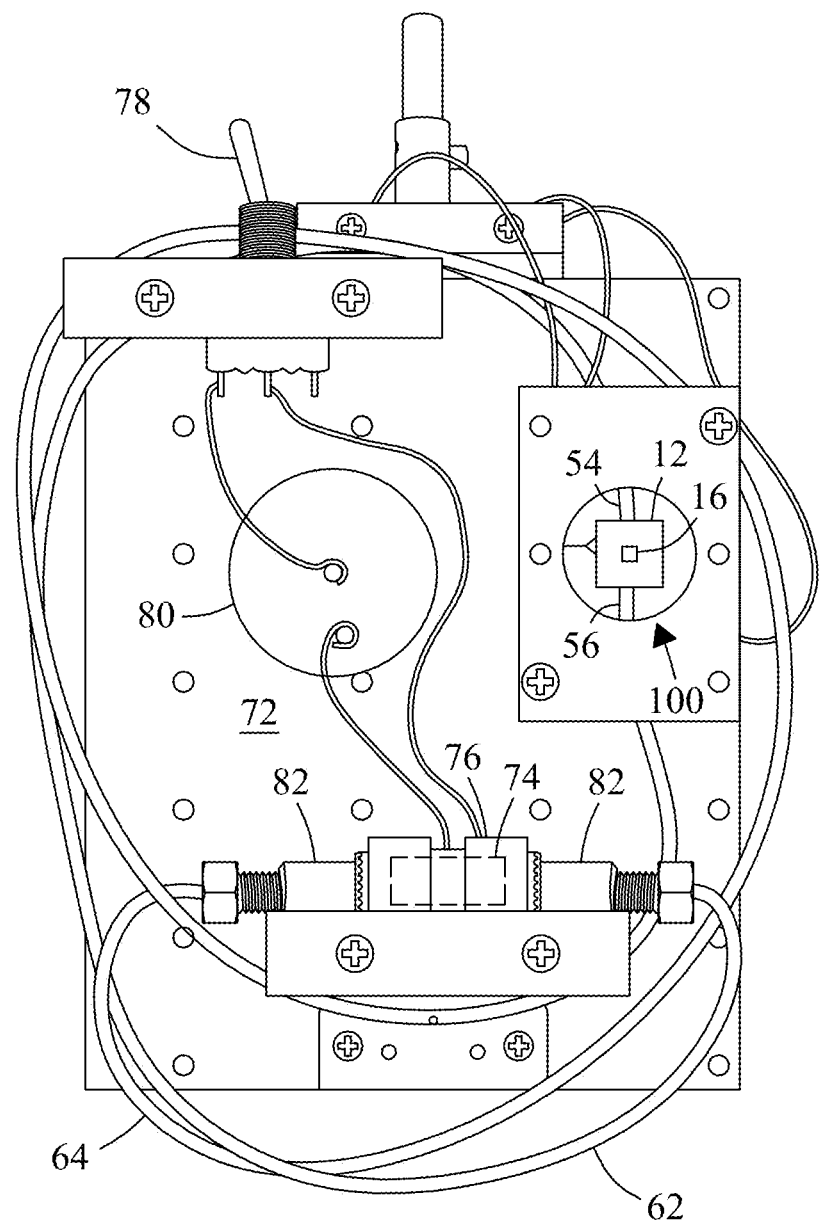
FIG. 5 is a photograph showing the microfluidic electrochemical device of the present invention coupled to a representative chemical imaging instrument.

FIG. 5 illustrates an assembled microfluidic electrochemical device (flow cell) 100 mounted to a ToF-SIMS stage 72 of a ToF-SIMS instrument (not shown). ToF-SIMS stage 72 may be configured to insert into a vacuum chamber (FIG. 1) of the ToF-SIMS instrument to provide chemical imaging analysis of liquid samples introduced into the microfluidic flow chamber (FIG. 1) at the electrode-liquid interface in-situ. In the figure, top frame 12 and SiN support membrane 16 of electrochemical device (flow cell) 100 can be seen. Lateral resolution in the ToF-SIMS instrument may be from about 20 nm to about 40 nm. Vertical resolution may be about 1 nm. In the figure, ToF-SIMS stage 72 may include a pump 74 (e.g., a model #3000126 electro-osmotic pump, Dolomite, United Kingdom) that introduces liquid samples into microfluidic flow chamber (FIG. 1). Pump 74 may be enclosed, e.g., in a vacuum enclosure 76 constructed of, e.g., stainless steel or another suitable material. Fittings 82 that enclose pump 74 within vacuum enclosure 76 may be constructed of a selected engineering thermoplastic such as polyaryletherketone (PAEK) or polyether ether ketone (PEEK) that provide suitable mechanical and chemical resistance properties for high-temperature and engineering applications. Vacuum enclosure 76 allows pump 74 to operate in the vacuum chamber (FIG. 1) of a selected analytical probe instrument (not shown). Liquid samples may be introduced through flow tubing 62 through metal flow tube 54 into microfluidic flow chamber (FIG. 1). Liquid samples may be removed from the microfluidic flow chamber (FIG. 1) through metal flow tube 56 out through flow tubing 62. Flow tubing 62 and 64 (e.g., TEFLON tubing) provides flows of various samples including, but not limited to, e.g., buffer solutions, electrolytes, biological broths, cell media, and other liquid samples delivered into the flow chamber (FIG. 1). Pump 74 may be powered with a battery 80 [e.g., a lithium-thionyl chloride (Li—SOCl$_2$) battery, Saft America, Valdosta, Ga., USA]. A switch 78 may be used to power pump 74 when ToF-SIMS stage 72 is introduced into the vacuum chamber (FIG. 1) of the ToF-SIMS instrument (not shown).

Electrochemical Analysis

Figure 6:
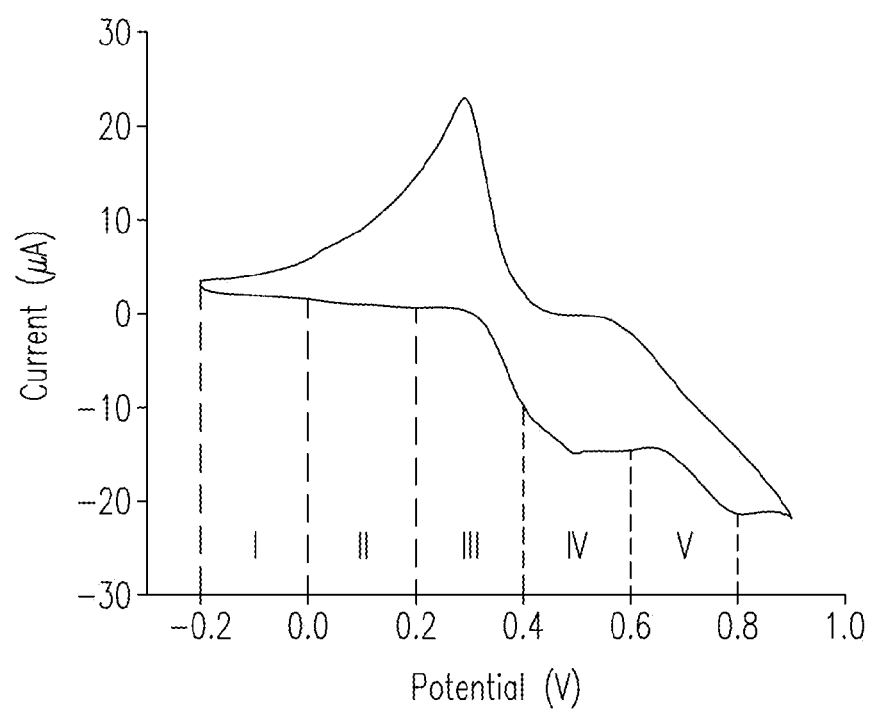
FIG. 6 shows a typical cyclic voltammogram obtained with the present invention.
Figure 7A:
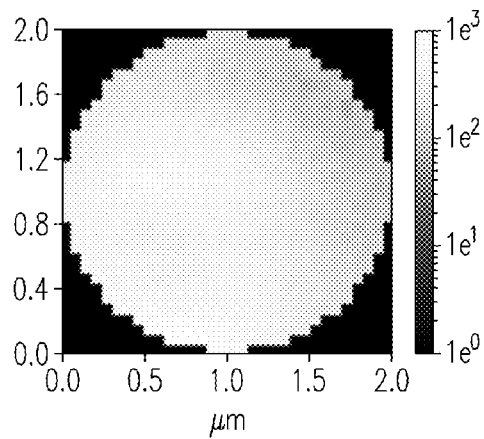
FIGS. 7a-7d show ToF-SIMS 2D chemical images of various ionic species acquired with the present invention.
Figure 7B:
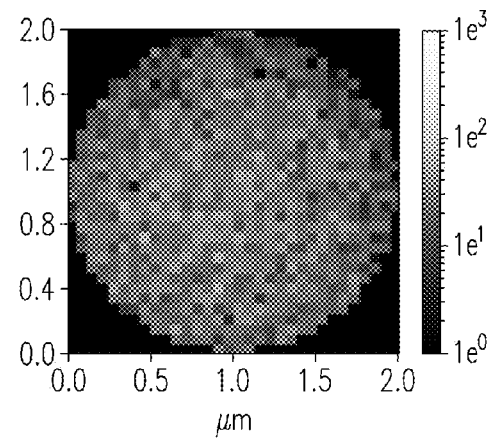
Figure 7C:
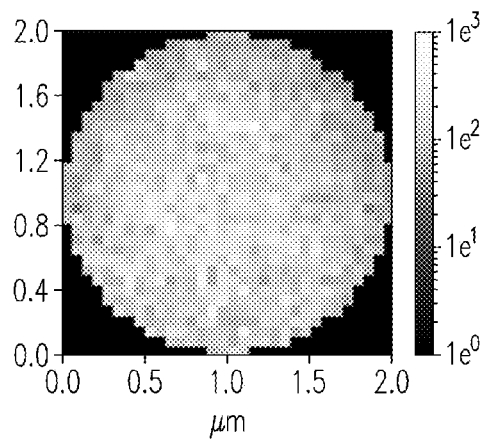
Figure 7D:
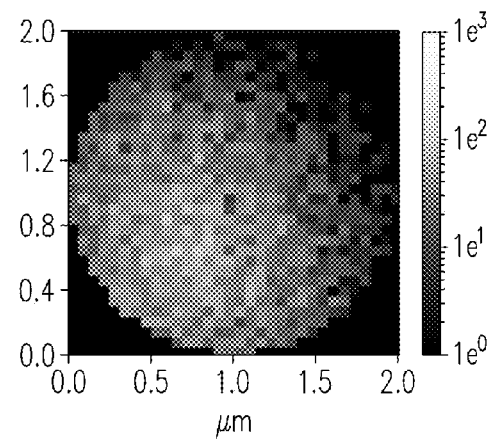

Electrochemical analysis may be provided by the present invention individually or simultaneously with chemical imaging analyses, as described above. An electrochemical workstation (FIG. 1) may be used to deliver potentials to electrodes (FIG. 1) of the microfluidic electrochemical device. FIG. 6 shows a typical cyclic voltammogram (CV) curve obtained from cyclic voltammetric (electrochemical) analyses. The CV curve obtained in high vacuum plots current (e.g., in μAmps) against potential (in Volts). Here, data were collected using a 10 mM KI electrolyte solution as a liquid sample at scan voltages ranging from −0.2 V to 0.9 V at a scan rate of 100 mV/s as measured by the gold (Au) working electrode (FIG. 3a). The CV curve collected at high vacuum has the same features as the CV curve obtained at ambient conditions. Results demonstrate the ability of the microfluidic electrochemical device to provide both electrochemical analysis and chemical imaging of chemical species (i.e., chemical speciation) positioned at selected depths and layers at surfaces of liquids, other flowable samples, and at the solid electrode-liquid interface. A slight potential shift in the CV curve may be due to differences in the selection of the reference electrode that do not affect performance of the microfluidic electrochemical device. Thus, no limitations are intended.

FIGS. 7a-7d show representative ToF-SIMS 2D images of the chemical species IO$_3^-$, I$_2^-$, I$_3^-$ and AuI$_2^-$ acquired at +0.8 V with the microfluidic electrochemical device of the present invention. ToF-SIMS is a representative instrument suitable for chemical imaging. Each pixel in the 2D images includes data corresponding to a spatial distribution of chemicals (including, e.g., transient species and chemical products) identified at the selected location or distance from the working electrode at the selected potential. Chemicals identified at the selected locations may be reflected in the m/z spectrum (see, e.g., discussion in reference to FIG. 8). Here, the working electrode was constructed of polycrystalline gold (Au) to allow direct electrochemical measurements at the electrode-solution interface. In the electrochemical process, electrons are removed from the metallic gold, and subsequent gold ions form strong complexes with iodide in the electrolyte (or gold iodide adlayers on the electrode) according to reaction [1]:

Reaction [1] is followed by four electrode reactions considered to be directly related to the total amount of chemisorbed iodine including solution redox, anodic oxidation of chemisorbed iodine, and iodate reduction as shown in reactions [2]-[5], respectively:

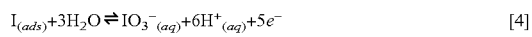

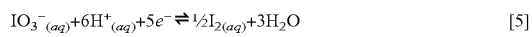

Figure 8:
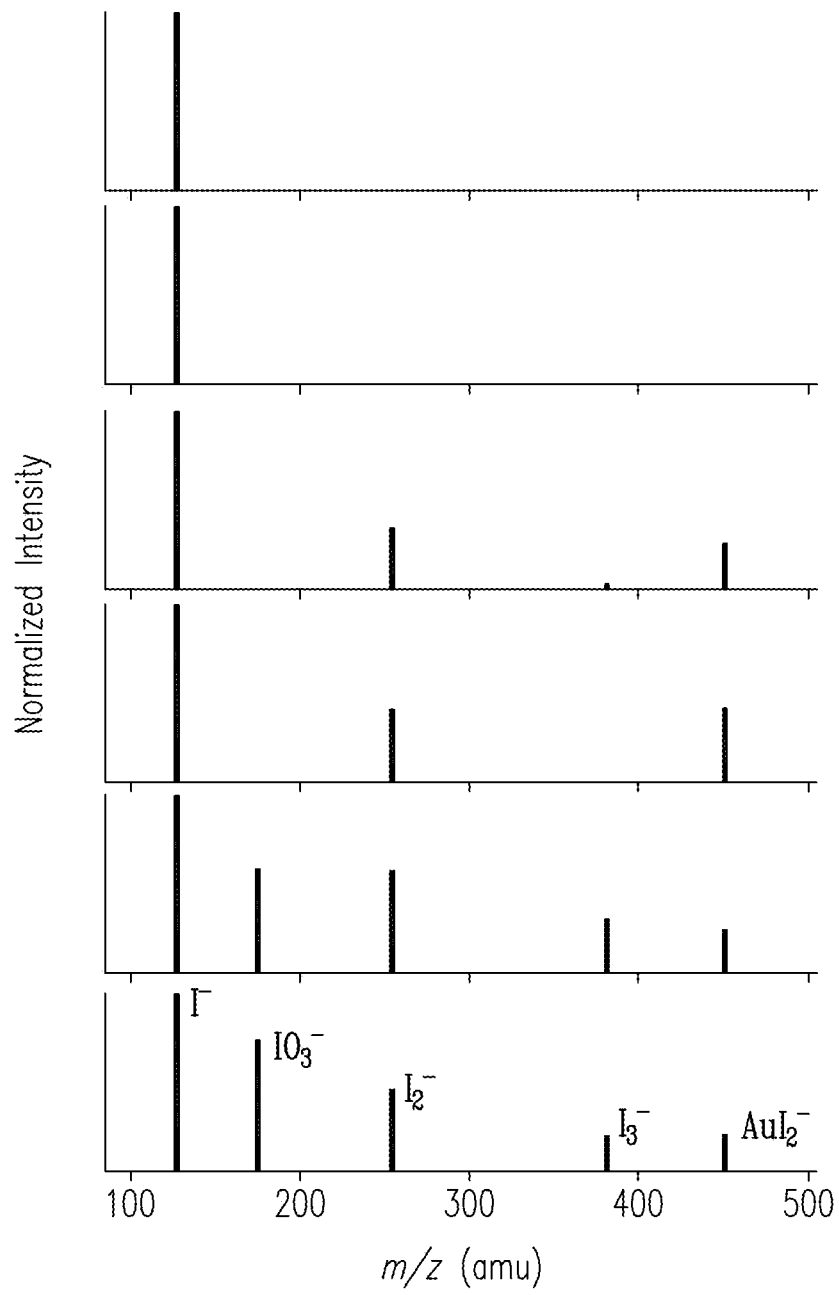
FIG. 8 shows ToF-SIMS m/z spectra acquired with the present invention at various voltages.

FIG. 8 presents ToF-SIMS m/z (chemical imaging) spectra that plot the normalized intensity as a function of the electrochemical (CV analysis) potential (from −0.2 V to 0.8 V, respectively) measured with a gold (Au) working electrode (FIG. 3a) in a supporting KI electrolyte. Iodine adlayers on surfaces of single crystal gold electrodes are known to exhibit various potential-dependent phase transitions that affect the underpotential deposition of metal ions on the electrode surfaces. "Underpotential Deposition (or UPD)" refers to a phenomenon in which metal cations are reduced to their solid metal form and are electrodeposited to the electrode surface at a potential that is less negative (and thus more electrochemically favored) than should normally occur at normal (or Nernst equilibrium) conditions. The observance of UPD is attributed to interactions between the metal ions to be electrodeposited and the metal on the electrode surface.

In the figure, only m/z peaks of interest are presented for clarity. Features of the CV are in agreement with reported literature values. Normalized ToF-SIMS m/z spectra obtained at different potentials clearly illustrate for the first time the molecular composition of the redox reaction products and intermediate species at different stages of the redox cycle. At −0.2 V, no redox reaction occurs. Thus, only I$^-$ is observed. The same is true at 0 V. Areas I and II (−0.2 V to +0.2 V) show formation of AuI$_2^-$, I$_2^-$, and I$_3^-$, respectively, which contrasts with reported literature results which indicate that no redox reaction occurs there. At +0.2 V, the complex AuI$_2^-$ as well as I$_2^-$ and I$_3^-$ are observed, indicating that reactions [1]-[3] occur in this region. Area III (i.e., +0.2 to +0.4 V) may reflect various equilibria species including, e.g., I$^-$, I$_2$, and I$_3^-$ corresponding to reactions [2] and [3]. At +0.4 V, no I$_3^-$ is observed, which is attributed to a redox reaction occurring at this voltage that favors dissociation of I$_3^-$. Area IV (i.e., +0.4 to +0.6 V) reflects oxidation of I$_2$ to IO$_3^-$ as given by reactions [2]-[4]. Area V (i.e., +0.6 to +0.8 V) reflects reduction of IO$_3^-$ to I$_2$, respectively. At +0.8 V, the expectation is that IO$_3^-$ can form. However, the ToF-SIMS m/z spectrum corresponding to the CV results indicates that IO$_3^-$ can form at lower potentials.

Applications

Microfluidic electrochemical devices of the present invention provide simultaneous chemical imaging and electrochemical analyses of chemical entities at the electrode-liquid (e.g., electrolyte) interface in-situ. In some embodiments, electrochemical devices of the present invention are portable, multimodal lab-on-a-chip devices. The present invention can, for the first time, provide combined electrochemical analyses and chemical imaging of electrode-liquid (or other solid-liquid) interfaces in concert with surface-sensitive vacuum techniques such as ToF-SIMS under vacuum conditions in-situ.

In various embodiments, the present invention has many varied and potential applications for study of a wide variety of analytes in liquid samples. The present invention provides measurement, determination, and/or characterization of various analytes including, but not limited to, e.g., redox-active analytes; biological analytes including, e.g., cells and bacteria; cell growth media; biofilms; chemical analytes; molecular analytes; solid analytes; mixtures; nanoparticles; complex analytes; transient analytes; battery electrolytes; buffer solutions; including combinations of these various analytes.

In some embodiments, electrode-electrolyte interactions in fluid motion in real time may be analyzed. Moreover, distributions of intermediate species in electrode-electrolyte reactions may be discerned using chemical imaging in real-time as reactions occur and potential-dependent surface changes may be followed in real-time in-situ. The following examples provide a further understanding of various aspects of the invention.

Example 1

Microfluidic Electrochemical Cell

The microfluidic electrochemical device was fabricated using a soft lithography approach. Exemplary dimensions of the electrochemical flow chamber were approximately 2.5 mm×2.5 mm×0.3 mm. The photomask was designed using AutoCAD software and printed with a mask printer (Intelligent Micro Patterning LLC, Model SF-100 Xpress). A template for casting the electrochemical flow chamber was made with SU-8 photoresist (Microchem, Newton, Mass.) on a silicon substrate. The template included a flow channel with a depth of 300 μm equal to the distance between the working electrode and a counter electrode. A 10:1 ratio (w/w) of polydimethylsiloxane (PDMS) prepolymer and curing agent (Sylgard 184, Dow Corning Co., Midland, Mich., USA) were thoroughly mixed, degassed under vacuum, poured onto the patterned template to a thickness of 1 cm, and cured in an oven at 75° C. overnight.

Example 2

Preparation of Potassium Iodide Sample Solutions

Aqueous 10 mM solutions of potassium iodide (Aldrich, 99.9%) were prepared in ultrapure water (18.2 MΩ·cm) obtained with a water purification system (Milli-Q Integral Water Purification System, EMD Millipore, Billerica, Mass., USA) at 25° C. Oxygen in the solutions was depleted using a nitrogen bubbler before filling the microfluidic electrochemical device. Solutions were degassed using a commercial degasser (e.g., a DU series 200 μL Degasys Ultimate internal volume degasser, Sanwa Tsusho Co., Ltd., Tokyo, Japan) to limit pressure build-up and bubble formation inside the device. The microfluidic electrochemical device was filled with solution using a syringe pump (Harvard apparatus, Holliston, Mass., USA).

Example 3

Operation in ToF-SIMS

The vacuum compatible microfluidic electrochemical device was deployed into a vacuum chamber of a commercial ToF-SIMS instrument (IONTOF GmbH, Munster, Germany). The microfluidic electrochemical device was checked for leaks in a vacuum chamber before usage. Vacuum pressure in the flow chamber of the electrochemical device during measurements was $2.0 \times 10^{-7}$ Torr to $5.5 \times 10^{-7}$ Torr. The ToF-SIMS instrument was configured to raster a focused (0.2 μm) primary ion beam through the SiN window of the electrochemical device over sample liquids. Ejected secondary ions were mass-analyzed to form surface chemical maps with a lateral resolution of about 0.2 μm. ToF-SIMS measurements were performed at a beam current of ~1.0 pA with a beam width of 125 ns and a repeated frequency of 16.7 kHz. ToF-SIMS provides molecular information, e.g., on the top layer (e.g., ~6 nm) of sample liquids and other solutions. ToF-SIMS may employ, e.g., 25 keV $Bi^+$ ions as probes. Ions were detected at from about 0 eV to about 10 eV. In the imaging mode, an area of $2 \times 2$ μm$^2$ was selected. The $Bi^+$ beam was scanned with 128×128 pixels with a total integration time of 295 seconds.

Example 4

Electrolyte Solutions

In exemplary tests, electrolyte solutions were used to demonstrate real-time observation of chemical species formed as a result of redox reactions in the microfluidic electrochemical flow device, e.g., the gold iodide adlayer at the surface of the electrolyte in contact with the working electrode in-situ. Electrolytes were simultaneously analyzed using cyclic voltammetry (CV) and Time-of-Flight Secondary Ion Mass Spectrometry (e.g., ToF-SIMS). Potential-dependent changes at the electrode surface and the electrolyte composition are characterized by ToF-SIMS imaging that reflect progression of electrochemical redox reactions as a function of time. Electrochemical results and ToF-SIMS m/z spectra obtained at different potentials show for the first time the gold adlayer and transient species formed during charge-transfer processes in-situ, as detailed herein.

Example 5

Cyclic Voltammograms

Cyclic voltammograms (CVs) were collected using an electrical-chemical station (Model 824 Electrochemical Detector, CH Instruments, Inc., Austin, Tex., USA). The reference electrode was a 200 nm Pt thin film. Voltammograms were collected at ambient and high vacuum ($<5 \times 10^{-7}$ Torr) conditions in an electrolyte at 25° C. performed at a scan rate of 20 mV/s. The scan was initiated at −0.2V. Potential was advanced at a step of 0.2V from −0.2 V to 0.9 V. Each voltage was held for a selected non-limiting time. ToF-SIMS data were also acquired. FIG. 6 shows a typical cyclic voltammogram obtained in concert with the present invention as a function of applied voltage. FIG. 8 shows representative ToF-SIMS m/z spectra acquired in-situ at various voltages in concert with the present invention.

Example 6

Analysis of Battery Electrolytes

The microfluidic electrochemical device of FIG. 1 may be used with a working electrode constructed of a sputter-deposited metal or metal oxide positioned on the backside of the SiN membrane. An (e.g., 1M) electrolyte may be injected into the electrochemical device via a syringe pump. An electrochemical station may be coupled to the microfluidic electrochemical device to apply various potentials between the working electrode (e.g., gold electrode) and counter electrode within the microfluidic electrochemical device to induce electron transfer within the electrolyte in the flow chamber. Electrolytes may be analyzed in either static or dynamic flow mode. During electrochemical analysis, a ToF-SIMS or other surface-sensitive analytical instrument may be used to simultaneously probe the surface of the electrode and electrolyte interface. Results similar to FIG. 6 and FIG. 8 may be obtained. The m/z data and charge/discharge curves acquired as a function of time and potential may be used to provide chemical imaging of chemical species such as complexes formed from charge transfer reactions at electrode and electrolyte surfaces that characterize the electrolyte and elucidate battery performance at the molecular scale, e.g., for battery applications that enables design of better electrode materials.

Example 7

Analysis of Biofilms

Figure 9:
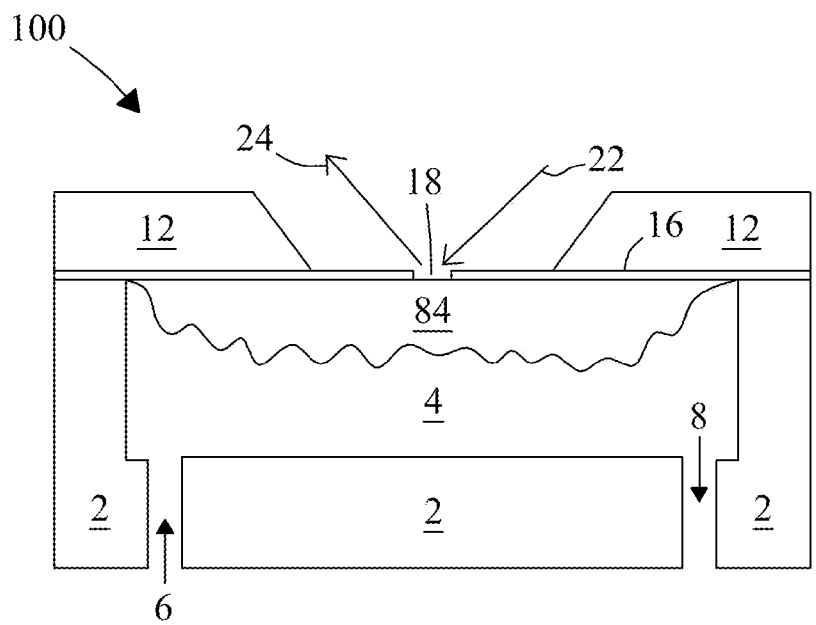
FIG. 9 shows another configuration of the present invention for analysis of biofilms.

FIG. 9 shows microfluidic device 100 of the present invention configured as a growth reactor for growth and analysis of biofilms. Biological broths may also be analyzed. In the figure, microfluidic device (reactor) 100 includes a flow chamber 2 configured with a top frame 12 (e.g., a silicon frame), a support membrane 16 (e.g., a SiN support membrane), a detection aperture 18, and a flow channel 4 through flow chamber 2 that connects to an inlet channel (inlet) 6 and outlet channel (outlet) 8. Flow chamber 2 may be constructed of, e.g., a PDMS elastomer as described previously herein in reference to FIG. 1. Fluid inlet 6 into reactor 100 and fluid outlet 8 out of reactor 100 was connected to PFTE tubing (FIG. 4 and FIG. 5) to provide a fluid flow path through microfluidic flow chamber 2. A needle was inserted into the inlet tubing, and reactor 100 was coupled to a custom-made manifold (not shown) that allowed delivery of the sample medium and other solutions into and out of reactor 100. A 70% ethanol solution was flowed through flow chamber 2 for three hours to sanitize microfluidic flow channel 4 and flow chamber 2. A minimum of five volume changes of filtered water (>18.2 MΩ) was then flowed to flush the ethanol solution from flow chamber 2. Two syringes (not shown) were used as fluid reservoirs to provide a sufficient quantity and flow of growth medium through reactor 100 to grow biofilm 84 without changing the supply of growth medium and other solutions. The manifold was connected to microfluidic reactor 100 via the needle. A sterile growth medium was flowed through flow chamber 4 overnight prior to inoculating reactor 100.

Biofilm growth may follow biofilm growth guidelines detailed, e.g., by McLean et al. in *J. Microbiol Methods* 74: 47-56). A late-log phase bacterial culture was harvested by centrifugation (5000×g, 10 minutes) and resuspended in an equal volume of sterile medium. One milliliter (1 mL) of the resuspended bacterial culture medium was flown through microfluidic reactor 100 via syringe (not shown) to inoculate reactor 100. The syringe was then exchanged with two syringes containing sterile growth medium. Flow mode was used during growth of biofilm 84. Cell growth medium was flowed at room temperature through microfluidic reactor 100 for five to six days at a flow rate permissive for sub-oxic bacterial growth to form a biofilm 84 on the underside of support membrane 16 below detection aperture 18. Biofilm 84 growth was monitored in real-time using a confocal microscope or other light microscope. Biofilm 84 achieved an average depth of 300 μm and a non-limiting width and length dimension of 500 μm. Static mode may be employed after growth of the biofilm 84 during chemical imaging. After growth of the biofilm 84, microfluidic reactor 100 containing the hydrated biofilm 84 was assembled onto a portable ToF-SIMS stage (FIG. 5) and introduced into the vacuum chamber (FIG. 1) of a ToF-SIMS instrument (or other analytical instruments) for chemical imaging in-situ. ToF-SIMS has an advantage in that it provides molecular recognition for biological (and other organic) molecules. Peaks (m/z) representing quasi molecular ions formed from loss of a hydrogen (e.g., [M-H]$^-$) are commonly observed in the ToF-SIMS spectra in negative mode. Electrodes described in reference to FIG. 1 may also be introduced into flow chamber 2 to provide combined electrochemical analysis and chemical imaging of biofilms 84 grown in microfluidic reactor 100, as well as cell media or biological broth media. Biofilm 84 and the cell medium (not shown) were imaged using a primary probe beam 22. Mass spectrometry ion data were collected with a secondary ion beam 24.

Figure 10A:
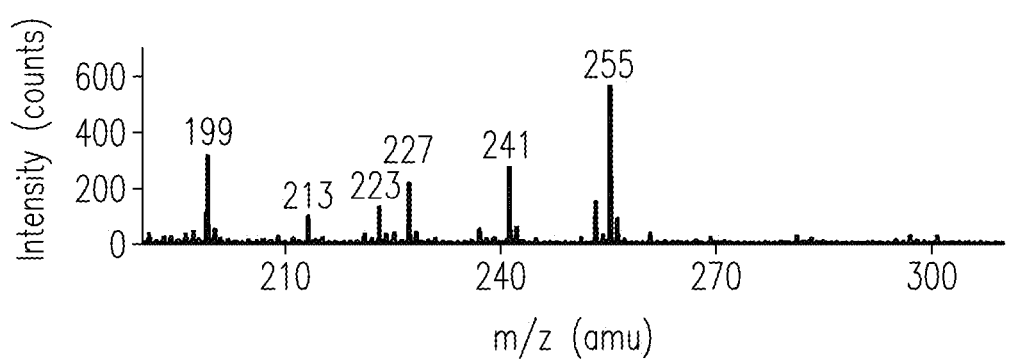
FIGS. 10a-10c present chemical imaging data for an exemplary biofilm grown and analyzed with the present invention.
Figure 10B:
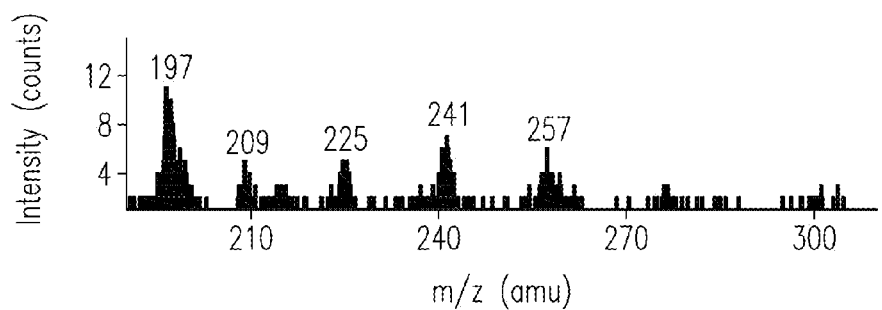
Figure 10C:
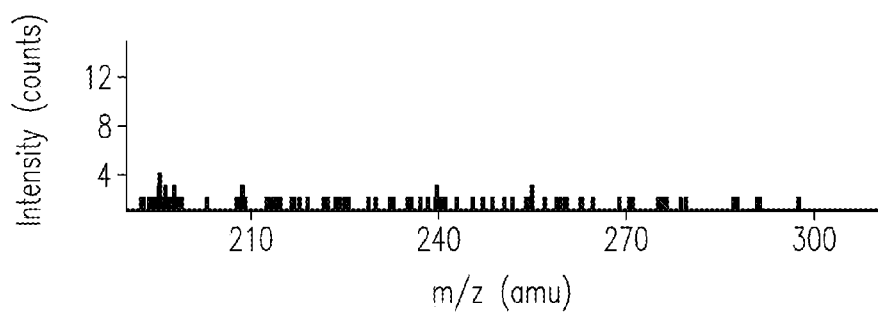

FIG. 10a presents a negative ToF-SIMS m/z spectrum showing characteristic fragment peaks for a dry *Shewanella* biofilm sample placed on a clean silicon wafer. FIG. 10b presents a negative ToF-SIMS m/z spectrum showing characteristic fragment peaks for the hydrated *Shewanella* biofilm grown in the microfluidic reactor chamber in-situ. The ToF-SIMS spectrum shows characteristic m/z peaks for selected fatty acids fragments including, e.g., $C_{14}$ fatty acid fragments (m/z of 227) and $C_{15}$ fatty acid fragments (m/z 241). Differences are observed between the liquid sample as compared to the dry sample. For example, additional peaks are observed for the liquid sample in the m/z range between 200 amu and 300 amu. FIG. 10c shows a ToF-SIMS m/z spectrum collected for the growth medium in the microfluidic channel acquired as a control. TABLE 1 lists peak (m/z) assignments and identities of selected fatty acid fragments observed in FIGS. 10a-10b.

TABLE 1 compares peak (m/z) assignments for fatty acid fragments identified from ToF-SIMS chemical imaging analyses of biofilm samples acquired with the microfluidic reactor of the present invention with theoretical peak assignments obtained from the LIPID MAPS Structure Database (LMSD).

| Name | Species | Formula | Peak (m/z) | LMSD (m/z) |
|---|---|---|---|---|
| Lauric acid | [M-H]– | $C_{12}H_{23}O_2^-$ | 199.14 | 199.17 |
| Tridecylic acid | [M-H]– | $C_{13}H_{25}O_2^-$ | 213.15 | 213.19 |
| Myristic acid | [M-H]– | $C_{14}H_{27}O_2^-$ | 227.16 | 227.20 |
| Pentadecylic acid | [M-H]– | $C_{15}H_{29}O_2^-$ | 241.18 | 241.22 |
| Palmitic acid | [M-H]– | $C_{16}H_{31}O_2^-$ | 255.18 | 255.23 |

Characteristic peaks at m/z values of 199, 213, 227, 241, and 255 were found in the dry biofilm sample corresponding to various fatty acid fragments. The peak at an m/z value of 199 was attributed to $C_{12}H_{23}O_2^-$ (Lauric acid). The peak at an m/z value of 213 was attributed to $C_{13}H_{25}O_2^-$ (Tridecylic acid). The peak at an m/z value 227 was attributed to $C_{14}H_{27}O_2^-$ (Myristic acid). The peak at an m/z value 241 was attributed to $C_{15}H_{29}O_2^-$ (Pentadecylic acid). The peak at an m/z value 255 was attributed to $C_{16}H_{31}O_2^-$ (Palmitic acid). Slight shifts in m/z values for fatty acid fragments reported here when compared to peaks in the LIPID MAPS Structure Database (LMSD) [www.lipidmaps.org] may be attributed to instrument systematic differences and the different strains of bacteria analyzed. In FIG. 10b, the hydrated (wet) biofilm sample shows more peaks when compared to the dry biofilm sample. Slight m/z shifts are attributed to instrument responses for a given experiment. For example, the 199 mass peak for lauric acid ($[C_{12}H_{23}O_2]^-$) is observed at 199.14 amu, which is consistent with the theoretical value (199.17 amu). And, the 213 mass peak for tridecylic acid ($[C_{13}H_{25}O_2]^-$) is observed at 213.15 amu, in good agreement with its theoretical value (213.19 amu). In the control experiment (FIG. 10c), no discernible peaks were found, which demonstrates that peaks observed for the dry biofilm sample and the wet biofilm sample stem are due to the biofilm. Resolution and intensity of peaks in the liquid biofilm sample may be increased by optimization of analysis parameters.

Figure 11A:
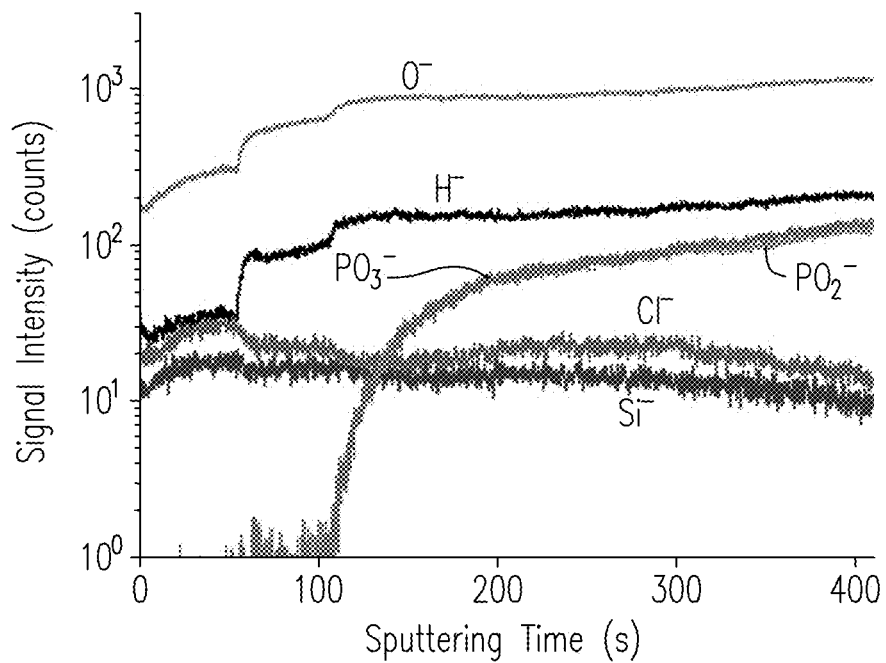
FIGS. 11a-11c present chemical imaging data from analysis of biofilms acquired with the present invention.
Figure 11B:
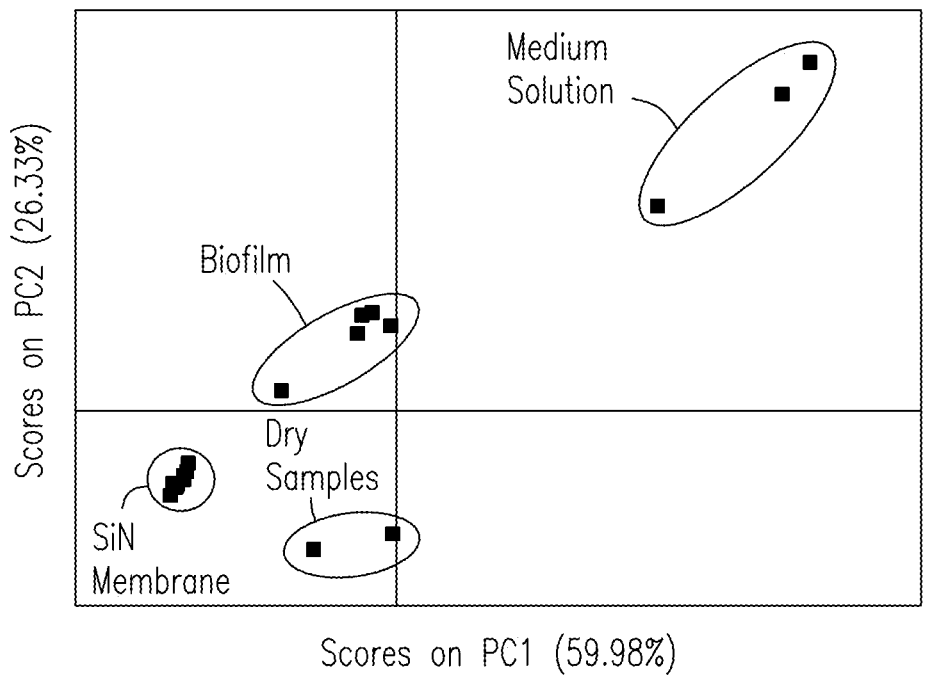
Figure 11C:
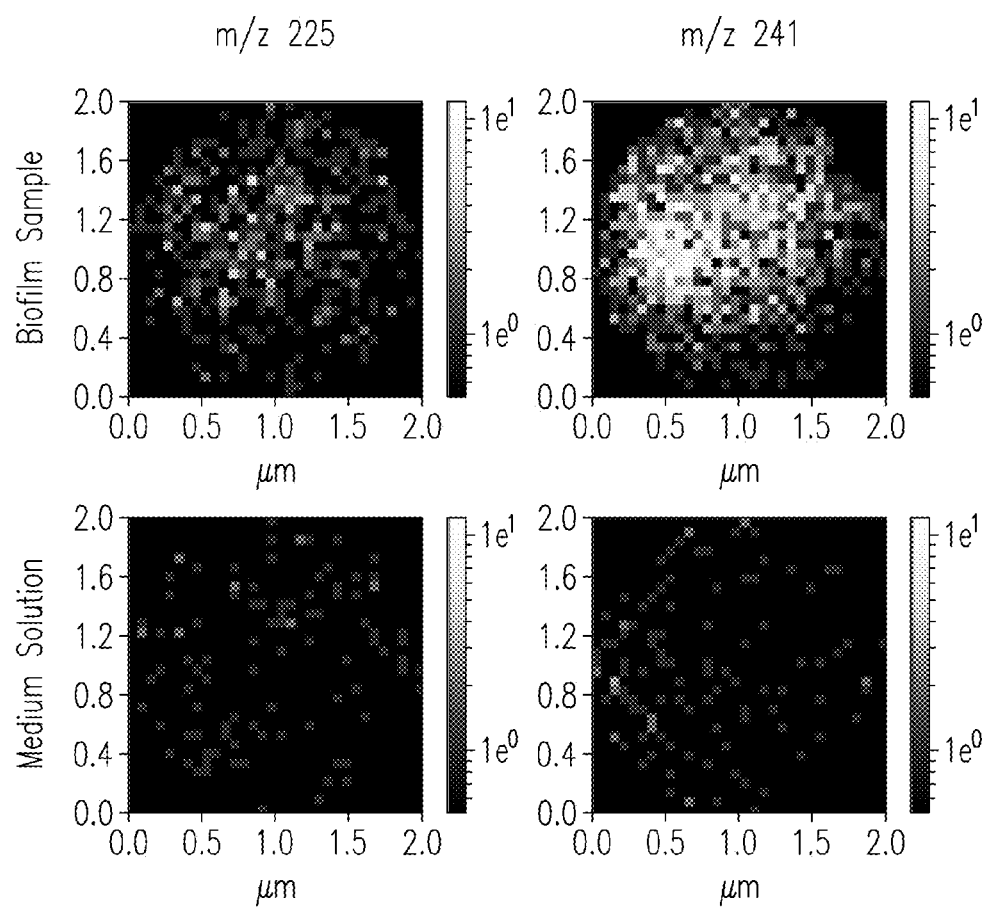

FIG. 11a shows ToF-SIMS depth profiles of key components in the hydrated biofilm sample. FIG. 11b shows principle component analysis (PCA) results that compare distinctions between the hydrated biofilm, the cell growth medium, the dry biofilm sample, and the SiN membrane of the microfluidic device. FIG. 11c shows 2D chemical images of fragments obtained from the biofilm and for the growth medium at an m/z 227 ($C_{14}$ fatty acid) and fragments at an m/z of 241 ($C_{15}$ fatty acid), respectively.

Example 8

Buffer Solution Analysis

The microfluidic electrochemical device of FIG. 1 was used. Three protein-modified gold nanoparticle containing solutions (SPI Supplies LLC, West Chester, Pa., USA) were tested. Proteins were goat anti-mouse IgG (H+L), goat anti-rabbit IgG, and Strepavidin, respectively. Gold nanoparticles had a mean diameter of, e.g., ~5 nm. Nanoparticles were suspended in 20 mM Tris/NaCl buffer, and diluted with deionized water to a concentration of 4 µg/mL. Solutions were introduced into the microfluidic device with a syringe pump (Harvard apparatus, Holliston, Mass.). Aqueous solutions were degassed by a commercial vacuum degasser (Chrom Tech, Inc., MN, USA). Wet nanoparticle samples were prepared by depositing a drop of a solution on a clean silicon wafer [e.g., a Si(100) wafer, University Wafer, Boston, Mass., USA]. Dry samples were prepared by drying a wet sample deposited on a silicon substrate (e.g., clean silicon wafers) under ambient conditions. Vacuum pressure in the microfluidic flow chamber was between about $2\times10^{-7}$ mbar to about $4\times10^{-7}$ mbar. Pressure increased during measurements to between about $3\times10^{-7}$ mbar and about $5\times10^{-7}$ mbar. The narrow pressure range indicates that no release, spraying, or spreading of aqueous solutions occurs through the detection aperture. Both SEM and ToF-SIMS instruments were used to study wet and dry samples in the microfluidic device. Elemental composition from SEM and molecular identification of these samples by ToF-SIMS were obtained and compared.

While preferred embodiments of the present invention have been shown and described, it will be apparent to those of ordinary skill in the art that many changes and modifications may be made without departing from the invention in its true scope and broader aspects. Appended claims are therefore intended to cover all such changes and modifications as fall within the spirit and scope of the present invention.

What is claimed is:

1. An electrochemical device for combined electrochemical analysis and chemical imaging of analytes at an electrode-liquid sample interface in-situ under vacuum, comprising:
   an analytical instrument producing one or more probe beams;
   an electrochemical microfluidic flow chamber that defines a liquid flow path through the flow chamber, the flow chamber includes a support membrane with at least one detection aperture configured to expose a surface of a liquid sample containing one or more analytes to one or more probe beams delivered from analytical instrument when the liquid sample is introduced past the at least one detection aperture under vacuum, the one or more probe beams when delivered through the at least one detection aperture determines the one or more analytes at the surface of the liquid sample providing chemical imaging thereof;
   a working electrode configured to apply a selected potential into the liquid sample between the working electrode and a reference electrode that drives reactions of the one or more analytes in the liquid sample as a function of time, space, and/or potential; and
   a counter electrode configured to measure electrical current stemming from reactions involving the one or more analytes to provide electrochemical analysis and chemical imaging of the analytes in the liquid sample at the surface of the working electrode-sample interface in-situ.

2. The electrochemical device of claim 1, wherein the electrochemical device provides simultaneous electrochemical analysis and chemical imaging or individual electrochemical analysis and chemical imaging analyses of a surface of the liquid sample at a selected depth or a selected layer measured at the working electrode-sample interface.

3. The electrochemical device of claim 1, further including a workstation disposed external to the electrochemical device configured to deliver the potential between the working electrode and reference electrode and to measure the current between the working electrode and the counter electrode.

4. The electrochemical device of claim 1, wherein the electrodes have a form selected from wires, thin films, and sputter-deposited thin films comprising metals, metal oxides, carbon, graphene, and combinations thereof.

5. The electrochemical device of claim 1, wherein the working electrode and the counter electrode are integrated with a reference electrode on a single substrate.

6. The electrochemical device of claim 1, wherein the counter electrode and the reference electrode are disposed on a substrate different from the substrate containing the working electrode.

7. The electrochemical device of claim 1, wherein the working electrode is disposed above the flow channel beneath the detection aperture and the counter electrode and the reference electrode are disposed below the flow channel in the electrochemical flow chamber.

8. The electrochemical device of claim 1, wherein the support membrane is composed of a material selected from: silicon nitride (SiN), silicon dioxide ($SiO_2$), or combinations thereof.

9. The electrochemical device of claim 1, wherein the electrochemical chamber includes one or more inlets and one or more outlets that deliver the liquid sample to and from the electrochemical chamber, respectively.

10. The electrochemical device of claim 9, wherein the inlets and the outlets include one or more branches.

11. The electrochemical device of claim 1, wherein the electrochemical chamber includes a flow channel with a depth in the range from about 0.1 μm to about 1000 μm.

12. The electrochemical device of claim 1, wherein the electrochemical flow chamber is disposed on a silicon substrate in the form of a silicon wafer or a silicon chip.

13. The electrochemical device of claim 1, wherein the electrochemical device is coupled operatively to an analytical instrument selected from the group consisting of: X-ray photoelectron spectroscopy (XPS); scanning electron microscopy (SEM); secondary ion mass spectrometry (SIMS); helium ion microscopy (HeIM); Auger electron spectroscopy (AES); Rutherford backscattering spectrometry (RBS); transmission electron microscopy (TEM), and combinations thereof that provides simultaneous electrochemical analysis and chemical imaging when a sample is introduced into the electrochemical device.

14. A method for combined electrochemical analysis and chemical imaging of analytes present at a working electrode-liquid sample interface in-situ under vacuum, comprising:
introducing a liquid sample containing one or more analytes in a liquid flow path defined through a microfluidic flow chamber of a microfluidic electrochemical device;
delivering a selected potential between a working electrode and a reference electrode in the microfluidic flow chamber to drive reactions of the one or more analytes in the liquid sample as a function of time, space, and/or potential;
exposing the liquid sample to at least one probe beam from at least one analytical instrument under vacuum to provide chemical imaging of chemical and molecular species stemming from reactions of the one or more analytes at a selected depth or a selected layer of the liquid sample at the working electrode-liquid interface in-situ; and
measuring electrical current between the working electrode and a counter electrode to provide electrochemical analysis of chemical and molecular species stemming from reactions of the one or more analytes at the selected depth or layer of the liquid sample to provide chemical imaging and electrochemical analysis of the chemical and molecular species at the working electrode-liquid sample interface in-situ.

15. The method of claim 14, wherein the liquid sample is an electrolyte solution or includes an electrolyte.

16. The method of claim 14, wherein the liquid sample is a buffer solution or includes a buffer.

17. The method of claim 14, wherein the microfluidic electrochemical device is configured as a bioreactor for growth and analysis of biofilms.

18. The method of claim 14, wherein the liquid sample is a biological medium containing one or more biological analytes selected from: cells, bacteria, biofilm precursors, or combinations thereof.

19. The method of claim 14, wherein the potential is delivered from, and current is measured by, an electrochemical workstation disposed external to the microfluidic electrochemical device.

20. The method of claim 14, wherein the method includes simultaneous or individual electrochemical analysis by cyclic voltammetry and chemical imaging by an analytical method selected from the group consisting of: X-ray photoelectron spectroscopy (XPS); scanning electron microscopy (SEM); secondary ion mass spectrometry (SIMS); helium ion microscopy (HeIM); Auger electron spectroscopy (AES); Rutherford backscattering spectrometry (RBS); transmission electron microscopy (TEM), and combinations thereof.

21. The method of claim 14, wherein the method includes chemically imaging adsorbed molecules at the surface of the working electrode and/or in the liquid adjacent the working electrode in-situ.

22. The method of claim 14, wherein the method includes following compositional changes of an electrolyte as a function of time in-situ.

23. The method of claim 14, wherein the method includes a time-resolved and/or a space-resolved determination of reaction products and intermediate chemical species as electron transfer occurs in the sample in-situ.

24. The method of claim 14, wherein the method includes electrochemically determining and chemically imaging material changes to an electrode in a microfluidic electrochemical device as potential is varied.

* * * * *